US008324166B2

(12) United States Patent
Gozes et al.

(10) Patent No.: US 8,324,166 B2
(45) Date of Patent: Dec. 4, 2012

(54) NEUROPROTECTION USING NAP-LIKE AND SAL-LIKE PEPTIDE MIMETICS

(75) Inventors: Illana Gozes, Ramat-Hasharon (IL); Alistair Stewart, Vancouver (CA); Maya Maor, Petach-Tikva (IL); Sharon Furman-Assaf, Tel Aviv (IL)

(73) Assignees: Ramot at Tel-Aviv University, Ltd., Tel-Aviv (IL); Allon Therapeutics, Inc., Vancouver, BC (CA)

( * ) Notice: Subject to any disclaimer, the term of this patent is extended or adjusted under 35 U.S.C. 154(b) by 338 days.

(21) Appl. No.: 12/708,384

(22) Filed: Feb. 18, 2010

(65) Prior Publication Data

US 2010/0216723 A1 Aug. 26, 2010

Related U.S. Application Data

(63) Continuation-in-part of application No. PCT/CA2008/001497, filed on Aug. 22, 2008.

(60) Provisional application No. 60/957,790, filed on Aug. 24, 2007.

(51) Int. Cl.
*A61K 38/08* (2006.01)
(52) U.S. Cl. .................. 514/17.7; 514/21.7; 530/328
(58) Field of Classification Search .................. None
See application file for complete search history.

(56) References Cited

U.S. PATENT DOCUMENTS

| | | | |
|---|---|---|---|
| 6,174,862 B1 | 1/2001 | Brenneman et al. | |
| 6,613,740 B1 | 9/2003 | Gozes et al. | |
| 6,649,411 B2 | 11/2003 | Gozes et al. | |
| 6,933,277 B2 | 8/2005 | Brenneman et al. | |
| 7,264,947 B2 | 9/2007 | Gozes et al. | |
| 7,384,908 B1 | 6/2008 | Brenneman et al. | |
| 7,427,590 B2 | 9/2008 | Brenneman et al. | |
| 7,427,598 B2 | 9/2008 | Spong et al. | |
| 7,452,867 B2 | 11/2008 | Gozes et al. | |
| 7,863,247 B1 | 1/2011 | Brenneman et al. | |
| 2005/0196754 A1* | 9/2005 | Drmanac et al. ............ 435/6 |
| 2007/0054847 A1 | 3/2007 | Gozes et al. | |
| 2007/0142269 A1 | 6/2007 | Lee et al. | |
| 2008/0194488 A1 | 8/2008 | Gozes et al. | |
| 2009/0124543 A1 | 5/2009 | Gozes et al. | |
| 2009/0137469 A1 | 5/2009 | Gozes et al. | |
| 2009/0170780 A1 | 7/2009 | Gozes et al. | |
| 2009/0203615 A1 | 8/2009 | Spong et al. | |
| 2009/0247457 A1 | 10/2009 | Brenneman et al. | |

FOREIGN PATENT DOCUMENTS

| | | |
|---|---|---|
| WO | WO 00/27875 A2 | 5/2000 |
| WO | WO 01/12654 A2 | 2/2001 |
| WO | WO 01/75067 A2 | 10/2001 |
| WO | WO 01/75067 A3 | 10/2001 |
| WO | WO 01/90197 A1 | 11/2001 |

OTHER PUBLICATIONS

Supplemental European Search Report dated Apr. 18, 2011, issued in related European Application No. 08783406.5.
Bassan, H. et al., "The effects of vascular intrauterine growth retardation on cortical astrocytes," *The Journal of Maternal-Fetal and Neonatal Medicine*, 2009, pp. 1-6.
Brenneman, D.E. et al., "Activity-Dependent Neurotrophic Factor: Structure-Activity Relationships of Femtomolar-acting Peptides," *The Journal of Pharmacology and Experimental Therapeutics*, 1998, vol. 285, No. 2, pp. 619-627.
Friedhoff, P. et al., "Rapid Assembly of Alzheimer-like Paired Helical Filaments from Microtube-Associated Protein Tau Monitored by Fluorescence in Solution," *Biochemistry*, 1998, vol. 37, No. 28, pp. 10223-10230.
Gozes, I., "Activity-dependent neuroprotective protein: From gene to drug candidate," *Pharmacology & Therapeutics*, 2007, vol. 114, pp. 146-154.
International Search Report mailed on Dec. 4, 2008, for International Application No. PCT/CA2008/001497 filed on Aug. 22, 2008, 2 pages.
Mandel, S. et al., "Activity-dependent Neuroprotective Protein Constitutes a Novel Element in the SWI/SNF Chromatin Remodeling Complex," *The Journal of Biological Chemistry*, Nov. 23, 2007, vol. 282, No. 47, pp. 34448-34456.
Perez, M. et al., "The role of the VQIVYK peptide in tau protein phosphorylation," *Journal of Neurochemistry*, 2007, vol. 103, pp. 1447-1460.
Ramsden, M. et al., "Age-Dependent Neurofibrillary Tangle Formation, Neuron Loss, and Memory Impairment in a Mouse Model of Human Taupathy (P301L)," *The Journal of Neuroscience*, Nov. 16, 2005, vol. 25, No. 46, pp. 10637-10647.
Shiryaev, N. et al., "NAP protects memory, increases soluble tau and reduces tau hyperphosphorylation in a taupathy model," *Neurobiology of Disease*, 2009, vol. 34, pp. 381-388.
Toso, L. et al., "Learning enhancement with neuropeptides," *American Journal of Obstetrics & Gynecology*, 2006, vol. 194, pp. 1153-1159.
Von Bergen, M. et al., "Assembly of τ protein into Alzheimer paired helical filaments depends on a local sequence motif ($^{308}$VQIVYK$^{311}$) forming β structure," *PNAS*, May 9, 2000, vol. 97, No. 10, pp. 5129-5134.
Wilkemeyer, M.F. et al., "Differential effects of ethanol antagonism and neuroprotection in peptide fragment NAPVSIPQ prevention of ethanol=induced developmental toxicity," *PNAS*, Jul. 8, 2003, vol. 100, No. 14, pp. 8543-8548.
Wilkemeyer, M.F. et al., "Ethanol Antagonist Peptides: Structural Specificity without Stereospecificity," *The Journal of Pharmacology and Experimental Therapeutics*, 2004, vol. 309, No. 3, pp. 1183-1189.

* cited by examiner

*Primary Examiner* — Christina Bradley
(74) *Attorney, Agent, or Firm* — Kilpatrick Townsend & Stockton LLP

(57) ABSTRACT

This invention relates to NAP-like and SAL-like peptide mimetics, polypeptides, or small molecules derived from them, and their use in the treatment of neuronal dysfunction, neurodegenerative disorders cognitive deficits, neuropsychiatric disorders, and autoimmune disease.

10 Claims, 9 Drawing Sheets p < 0.0005 NAP vs. control; *** = p < 0.0005 NATLSIHQ vs. control;
** = p < 0.001 NATLSIHQ vs. control
The graph represents three independent experiments performed in quadruplicates.

Brain-Body weight ratio was calculated for each mouse and averaged per group
[TAU-Tg + NAT 0.0148+0.0009, TAU-Tg+Vh 0.0117+0.0007, w.t 0.0152+0.0005].

* Tukey HSD post-hoc test showed a significant difference between the NAT and vehicle treated TAU-Tg groups (p=0.030).

** Tukey HSD post-hoc test showed a significant difference between the non-Tg and the vehicle treated Tau-tg animals (p=0.007).

Figure 8

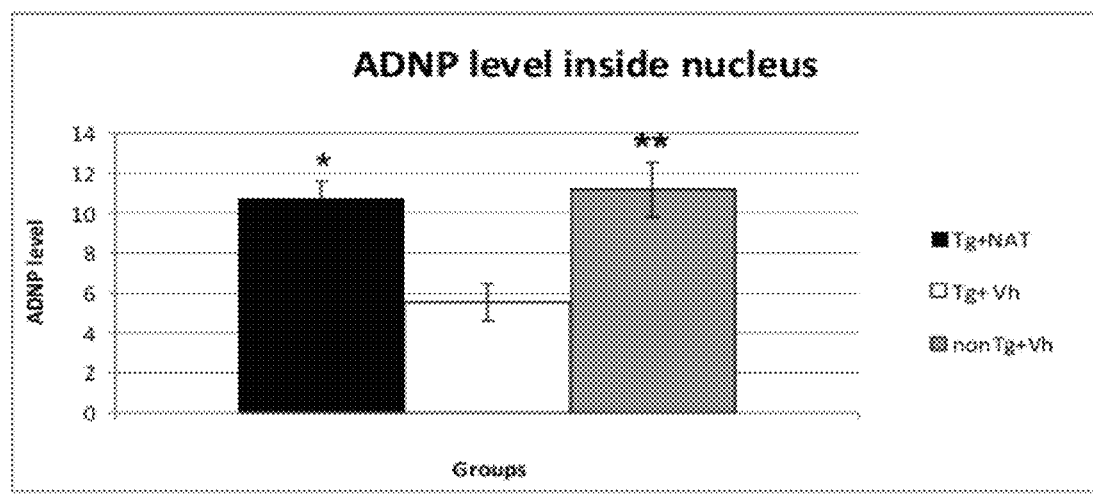

The ADNP amount in each band was calculated as percentage from the total amount of all bands. ADNP amounts of each group were averaged- TAU-Tg + NAT 10.747+0.839, TAU-Tg+Vh 5.52+0.92, w.t 11.17+1.35].

* Tukey HSD post-hoc test revealed a difference between the NAT and vehicle treated TAU-Tg groups (p=0.0028).
** Tukey HSD post-hoc test revealed a difference between the vehicle treated TAU-Tg and non-TG group (p=0.0097). Vh=vehicle.

The actin amount in each band was calculated as its percentage from the total amount of all bands. Actin amounts of each group were averaged- TAU-Tg + NAT 10.68+1.746, TAU-Tg+Vh 8.404+3.4, non-Tg 8.295+2.61.

SEQUENCE LISTING

```
<160> NUMBER OF SEQ ID NOS: 31

<210> SEQ ID NO 1
<211> LENGTH: 8
<212> TYPE: PRT
<213> ORGANISM: Artificial Sequence
<220> FEATURE:
<223> OTHER INFORMATION: synthetic NAP neuroactive peptide, NAP

<400> SEQUENCE: 1

Asn Ala Pro Val Ser Ile Pro Gln
 1               5

<210> SEQ ID NO 2
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 2

Asn Ala Val Leu Ser Ile His Gln
 1               5

<210> SEQ ID NO 3
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 3

Asn Ala Thr Leu Ser Val His Gln
 1               5

<210> SEQ ID NO 4
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 4

Asn Ala Thr Leu Ser Ile His Gln
 1               5

<210> SEQ ID NO 5
<211> LENGTH: 9
<212> TYPE: PRT
<213> ORGANISM: Artificial Sequence
<220> FEATURE:
<223> OTHER INFORMATION: synthetic NAP-like peptide

<400> SEQUENCE: 5

Asn Ala Thr Leu Ser Ile Val His Gln
 1               5

<210> SEQ ID NO 6
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 6

Ser Thr Pro Thr Ala Ile Pro Gln
```

```
<210> SEQ ID NO 7
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 7

Asn Thr Pro Val Ser Ile Pro Gln
 1               5

<210> SEQ ID NO 8
<211> LENGTH: 7
<212> TYPE: PRT
<213> ORGANISM: Artificial Sequence
<220> FEATURE:
<223> OTHER INFORMATION: synthetic NAP-like peptide

<400> SEQUENCE: 8

Ala Pro Val Ser Ile Pro Gln
 1               5

<210> SEQ ID NO 9
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 9

Asn Thr Pro Ile Ser Ile Pro Gln
 1               5

<210> SEQ ID NO 10
<211> LENGTH: 7
<212> TYPE: PRT
<213> ORGANISM: Artificial Sequence
<220> FEATURE:
<223> OTHER INFORMATION: synthetic NAP-like peptide

<400> SEQUENCE: 10

Asn Ala Pro Val Ser Ile Pro
 1               5

<210> SEQ ID NO 11
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 11

Asn Ala Pro Val Ala Val Pro Gln
 1               5

<210> SEQ ID NO 12
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 12

Asn Ala Arg Val Ser Ile Pro Gln
 1               5
```

```
<210> SEQ ID NO 13
<211> LENGTH: 8
<212> TYPE: PRT
<213> ORGANISM: Artificial Sequence
<220> FEATURE:
<223> OTHER INFORMATION: synthetic NAP-like peptide

<400> SEQUENCE: 13

Asp Ala Pro Val Ser Val Pro Gln
 1               5

<210> SEQ ID NO 14
<211> LENGTH: 8
<212> TYPE: PRT
<213> ORGANISM: Artificial Sequence
<220> FEATURE:
<223> OTHER INFORMATION: synthetic NAP-like peptide
<220> FEATURE:
<221> NAME/KEY: MOD_RES
<222> LOCATION: (2)...(2)
<223> OTHER INFORMATION: Xaa = any amino acid

<400> SEQUENCE: 14

Asn Xaa Pro Val Ser Ile Pro Gln
 1               5

<210> SEQ ID NO 15
<211> LENGTH: 8
<212> TYPE: PRT
<213> ORGANISM: Artificial Sequence
<220> FEATURE:
<223> OTHER INFORMATION: synthetic NAP-like peptide
<220> FEATURE:
<221> NAME/KEY: MOD_RES
<222> LOCATION: (2)...(2)
<223> OTHER INFORMATION: Xaa = any amino acid
<220> FEATURE:
<221> NAME/KEY: MOD_RES
<222> LOCATION: (4)...(4)
<223> OTHER INFORMATION: Xaa = Ile, Leu or Val

<400> SEQUENCE: 15

Asn Xaa Pro Xaa Ser Ile Pro Gln
 1               5

<210> SEQ ID NO 16
<211> LENGTH: 8
<212> TYPE: PRT
<213> ORGANISM: Artificial Sequence
<220> FEATURE:
<223> OTHER INFORMATION: synthetic NAP-like peptide
<220> FEATURE:
<221> NAME/KEY: MOD_RES
<222> LOCATION: (5)...(5)
<223> OTHER INFORMATION: Xaa = Ser or Thr
<220> FEATURE:
<221> NAME/KEY: MOD_RES
<222> LOCATION: (6)...(6)
<223> OTHER INFORMATION: Xaa = Ile, Leu or Val

<400> SEQUENCE: 16

Asn Ala Pro Val Xaa Xaa Pro Gln
 1               5

<210> SEQ ID NO 17
<211> LENGTH: 8
<212> TYPE: PRT
<213> ORGANISM: Artificial Sequence
<220> FEATURE:
<223> OTHER INFORMATION: synthetic NAP-like peptide
<220> FEATURE:
```

```
<221> NAME/KEY: MOD_RES
<222> LOCATION: (3)...(3)
<223> OTHER INFORMATION: Xaa = any amino acid

<400> SEQUENCE: 17

Asn Ala Xaa Val Ser Ile Pro Gln
 1               5

<210> SEQ ID NO 18
<211> LENGTH: 8
<212> TYPE: PRT
<213> ORGANISM: Artificial Sequence
<220> FEATURE:
<223> OTHER INFORMATION: synthetic NAP-like peptide
<220> FEATURE:
<221> NAME/KEY: MOD_RES
<222> LOCATION: (1)...(1)
<223> OTHER INFORMATION: Xaa = Asn or Gln
<220> FEATURE:
<221> NAME/KEY: MOD_RES
<222> LOCATION: (6)...(6)
<223> OTHER INFORMATION: Xaa = Ile, Leu or Val

<400> SEQUENCE: 18

Xaa Ala Pro Val Ser Xaa Pro Gln
 1               5

<210> SEQ ID NO 19
<211> LENGTH: 9
<212> TYPE: PRT
<213> ORGANISM: Artificial Sequence
<220> FEATURE:
<223> OTHER INFORMATION: synthetic SAL neuroactive peptide; SAL;
      ADNF-9; ADNF-1

<400> SEQUENCE: 19

Ser Ala Leu Leu Arg Ser Ile Pro Ala
 1               5

<210> SEQ ID NO 20
<211> LENGTH: 8
<212> TYPE: PRT
<213> ORGANISM: Artificial Sequence
<220> FEATURE:
<223> OTHER INFORMATION: synthetic SAL-like peptide

<400> SEQUENCE: 20

Ala Leu Leu Arg Ser Ile Pro Ala
 1               5

<210> SEQ ID NO 21
<211> LENGTH: 7
<212> TYPE: PRT
<213> ORGANISM: Artificial Sequence
<220> FEATURE:
<223> OTHER INFORMATION: synthetic SAL-like peptide

<400> SEQUENCE: 21

Ala Leu Leu Arg Ser Ile Pro
 1               5

<210> SEQ ID NO 22
<211> LENGTH: 8
<212> TYPE: PRT
<213> ORGANISM: Artificial Sequence
<220> FEATURE:
<223> OTHER INFORMATION: synthetic SAL-like peptide

<400> SEQUENCE: 22
```

```
Ala Met Leu Arg Ser Ile Pro Ala
 1               5
```

```
<210> SEQ ID NO 23
<211> LENGTH: 8
<212> TYPE: PRT
<213> ORGANISM: Artificial Sequence
<220> FEATURE:
<223> OTHER INFORMATION: synthetic SAL-like peptide

<400> SEQUENCE: 23

Ala Leu Leu Arg Ala Ile Pro Ala
 1               5
```

```
<210> SEQ ID NO 24
<211> LENGTH: 8
<212> TYPE: PRT
<213> ORGANISM: Artificial Sequence
<220> FEATURE:
<223> OTHER INFORMATION: synthetic SAL-like peptide

<400> SEQUENCE: 24

Ser Ala Leu Leu Arg Ser Ile Pro
 1               5
```

```
<210> SEQ ID NO 25
<211> LENGTH: 8
<212> TYPE: PRT
<213> ORGANISM: Artificial Sequence
<220> FEATURE:
<223> OTHER INFORMATION: synthetic SAL-like peptide

<400> SEQUENCE: 25

Ser Ala Leu Leu Arg Ala Ile Pro
 1               5
```

```
<210> SEQ ID NO 26
<211> LENGTH: 8
<212> TYPE: PRT
<213> ORGANISM: Artificial Sequence
<220> FEATURE:
<223> OTHER INFORMATION: synthetic SAL-like peptide

<400> SEQUENCE: 26

Ala Leu Leu Arg Thr Ile Pro Ala
 1               5
```

```
<210> SEQ ID NO 27
<211> LENGTH: 8
<212> TYPE: PRT
<213> ORGANISM: Artificial Sequence
<220> FEATURE:
<223> OTHER INFORMATION: synthetic SAL-like peptide

<400> SEQUENCE: 27

Ala Leu Leu Arg Ser Val Pro Ala
 1               5
```

```
<210> SEQ ID NO 28
<211> LENGTH: 8
<212> TYPE: PRT
<213> ORGANISM: Artificial Sequence
<220> FEATURE:
<223> OTHER INFORMATION: synthetic SAL-like peptide
<220> FEATURE:
<221> NAME/KEY: MOD_RES
<222> LOCATION: (2)...(2)
<223> OTHER INFORMATION: Xaa = Ile, Leu or Val
```

```
<400> SEQUENCE: 28

Ala Xaa Leu Arg Ser Ile Pro Ala
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic SAL-like peptide
<220> FEATURE:
<221> NAME/KEY: MOD_RES
<222> LOCATION: (5)...(5)
<223> OTHER INFORMATION: Xaa = Ser or Thr

<400> SEQUENCE: 29

Ala Leu Leu Arg Xaa Ile Pro Ala
1               5

<210> SEQ ID NO 30
<211> LENGTH: 8
<212> TYPE: PRT
<213> ORGANISM: Artificial Sequence
<220> FEATURE:
<223> OTHER INFORMATION: synthetic SAL-like peptide
<220> FEATURE:
<221> NAME/KEY: MOD_RES
<222> LOCATION: (6)...(6)
<223> OTHER INFORMATION: Xaa = Ser or Thr

<400> SEQUENCE: 30

Ser Ala Leu Leu Arg Xaa Ile Pro
1               5

<210> SEQ ID NO 31
<211> LENGTH: 8
<212> TYPE: PRT
<213> ORGANISM: Artificial Sequence
<220> FEATURE:
<223> OTHER INFORMATION: synthetic SAL-like peptide
<220> FEATURE:
<221> NAME/KEY: MOD_RES
<222> LOCATION: (6)...(6)
<223> OTHER INFORMATION: Xaa = Ile, Leu or Val

<400> SEQUENCE: 31

Ala Leu Leu Arg Ser Xaa Pro Ala
1               5
```

NEUROPROTECTION USING NAP-LIKE AND SAL-LIKE PEPTIDE MIMETICS

CROSS-REFERENCES TO RELATED APPLICATIONS

This application is a continuation-in-part of PCT/CA2008/001497, filed Aug. 22, 2008, which claims the benefit of U.S. Provisional Application No. 60/957,790, filed Aug. 24, 2007, the contents of all of the above are hereby incorporated by reference in the entirety for all purposes.

FIELD OF THE INVENTION

This invention relates to NAP-like and SAL-like peptide mimetics, polypeptides, or small molecules derived from them, and their use in the treatment of neuronal dysfunction, neurodegenerative disorders cognitive deficits, neuropsychiatric disorders, and autoimmune disease.

BACKGROUND OF THE INVENTION

NAP, an 8-amino-acid peptide (NAPVSIPQ, SEQ ID NO:1), is derived from activity-dependent neuroprotective protein, ADNP (U.S. Pat. No. 6,613,740; Bassan et al., *J. Neurochem.* 72: 1283-1293 (1999)). The NAP sequence within the ADNP gene is identical in rodents and humans (U.S. Pat. No. 6,613,740; Zamostiano, et al., *J. Biol. Chem.* 276:708-714 (2001)).

In cell cultures, NAP has been shown to have neuroprotective activity at femtomolar concentrations against a wide variety of toxins (Bassan et al., 1999; Offen et al., *Brain Res.* 854:257-262 (2000)). In animal models simulating parts of the Alzheimer's disease pathology, NAP was protective as well (Bassan et al., 1999; Gozes et al., *J. Pharmacol. Exp. Ther.* 293:1091-1098 (2000); see also U.S. Pat. No. 6,613,740). In normal aging rats, intranasal administration of NAP improved performance in the Morris water maze. (Gozes et al., *J. Mol. Neurosci.* 19:175-178 (2002)). Furthermore, NAP reduced infarct volume and motor function deficits after ischemic injury, by decreasing apoptosis (Leker et al., *Stroke* 33:1085-1092 (2002)) and reducing damage caused by closed head injury in mice by decreasing inflammation (Beni Adani et al., *J. Pharmacol. Exp. Ther.* 296:57-63 (2001); Romano et al., *J. Mol. Neurosci.* 18:37-45 (2002); Zaltzman et al., *NeuroReport* 14:481-484 (2003)). In a model of fetal alcohol syndrome, fetal death after intraperitoneal injection of alcohol was inhibited by NAP treatment (Spong et al., *J. Pharmacol. Exp. Ther.* 297:774-779 (2001); see also International PCT Application Publication No. WO 00/53217). Utilizing radiolabeled peptides these studies showed that NAP can cross the blood-brain barrier and can be detected in rodents' brains either after intranasal treatment (Gozes et al., 2000) or intravenous injection (Leker et al., 2002) or intraperitoneal administration (Spong et al., 2001).

SAL, a 9-amino acid peptide (SALLRSIPA, SEQ ID NO:19), also known as ADNF-9 or ADNF-1, was identified as the shortest active form of ADNF (see U.S. Pat. No. 6,174,862). SAL has been shown in in vitro assays and in vivo disease models to keep neurons of the central nervous system alive in response to various insults (e.g., Gozes et al., 2000; Brenneman et al., *J. Pharmacol. Exp. Ther.* 285:619-627 (1998)). D-SAL is an all D-amino acid derivative of SAL that is stable and orally available (Brenneman, et al., *J Pharmacol Exp Ther.* 309:1190-7 (2004)) and surprisingly exhibits similar biological activity (potency and efficacy) to SAL in the systems tested. ADNF-1 complexes are described in International PCT Application Publication No. WO03/022226.

Neuroactive peptides, such as NAP and SAL, appear to be extremely sensitive to even single-amino acid, conservative substitutions. See, e.g., Brenneman et al., *J. Pharm. Ex. Ther.*, 285:619-627 (1998) and Wilkemeyer et al., *Proc. Natl. Acad. Sci, USA,* 100:8543-8 (2003). Thus, while NAP and SAL are model neuroactive peptides, even conservative peptide variations of their core sequences are not predicted to be therapeutically effective. Accordingly, while there have been advances in this field, there remains a need for further neuroactive peptides. The present invention solves this and other needs.

BRIEF SUMMARY OF THE INVENTION

The present invention provides biologically active NAP-like peptide mimetics or SAL-like pepetide mimetics and methods to make and use these peptides. The formula of the NAP-like peptide mimetics or SAL-like pepetide mimetics is $(R^1)_a$—$(R^2)$—$(R^3)_b$. $R^1$ is an amino acid sequence comprising from 1 to about 40 amino acids wherein each amino acid is independently selected from the group consisting of naturally occurring amino acids and amino acid analogs. $R^2$ is one of the following sequences: NATLSIHQ (SEQ ID NO:4), STPTAIPQ (SEQ ID NO:6), NAVLSIHQ (SEQ ID NO:2), NATLSVHQ (SEQ ID NO:3), NATLSIVHQ (SEQ ID NO:5), NTPVSIPQ (SEQ ID NO:7), APVSIPQ (SEQ ID NO:8), NTPISIPQ (SEQ ID NO:9), NAPVSIP (SEQ ID NO:10), NAPVAVPQ (SEQ ID NO:11), NARVSIPQ (SEQ ID NO:12), DAPVSVPQ (SEQ ID NO:13), ALLRSIPA (SEQ ID NO:20), ALLRSIP (SEQ ID NO:21), AMLRSIPA (SEQ ID NO:22), ALLRAIPA (SEQ ID NO:23), SALLRSIP (SEQ ID NO:24), SALLRAIP (SEQ ID NO:25), ALLRTIPA (SEQ ID NO:26), and ALLRSVPA (SEQ ID NO:27). $R^3$ is an amino acid sequence comprising from 1 to about 40 independently selected amino acids, e.g., naturally occurring amino acids or amino acid analogs. a and b are independently selected and are equal to zero or one. The sequences NAPVSIPQ (SEQ ID NO:1) or SALLRSIPA (SEQ ID NO:19) are specifically excluded from this formula.

In one embodiment, the NAP-like peptide mimetic or SAL-like peptide mimetic includes a core sequence, i.e., $R^2$ selected from NATLSIHQ (SEQ ID NO:4) and STPTAIPQ (SEQ ID NO:6).

In another embodiment, the NAP-like peptide mimetic or SAL-like peptide includes only the core amino acid sequence, i.e., $R^2$. That is, a and b are equal to zero.

In one embodiment, the NAP-like peptide mimetic or SAL-like peptide includes at least one D-amino acid in the core amino acid sequence, i.e., $R^2$.

In one embodiment, each amino acid of the NAP-like peptide mimetic or SAL-like peptide, i.e., $R^2$, is a D-amino acid.

In another embodiment, the NAP-like peptide mimetic or SAL-like peptide mimetic includes at least one protecting group.

In one embodiment, the NAP-like peptide mimetic or SAL-like peptide mimetic includes the core amino acid sequence NATLSIHQ (SEQ ID NO:4). In a further embodiment, the NAP-like peptide mimetic or SAL-like peptide mimetic consists of the core amino acid sequence NATLSIHQ (SEQ ID NO:4). In a further embodiment, the core amino acid sequence NATLSIHQ (SEQ ID NO:4) includes at least one D-amino acid. In another embodiment, each amino acid of the core amino acid sequence NATLSIHQ (SEQ ID NO:4) is a D-amino acid.

In one embodiment, the NAP-like peptide mimetic or SAL-like peptide mimetic includes the core amino acid sequence STPTAIPQ (SEQ ID NO:6). In a further embodiment, the NAP-like peptide mimetic or SAL-like peptide mimetic consists of the core amino acid sequence STPTAIPQ (SEQ ID NO:6). In a further embodiment, the core amino acid sequence STPTAIPQ (SEQ ID NO:6) includes at least one D-amino acid. In another embodiment, each amino acid of the core amino acid sequence STPTAIPQ (SEQ ID NO:6) is a D-amino acid.

In another aspect, the invention provides a pharmaceutical composition includes a NAP-like peptide mimetic or SAL-like peptide mimetic with the formula described above. The pharmaceutical composition can also include a second neuroprotective polypeptide such as a neuroprotective polypeptide comprising NAPVSIPQ (SEQ ID NO:1) or SALLRSIPA (SEQ ID NO:19).

In another aspect the invention provides a method of treating or preventing a neurodegenerative disorder, a cognitive deficit, an autoimmune disorder, peripheral neurotoxicity, motor dysfunction, sensory dysfunction, anxiety, depression, schizophrenia, psychosis, a condition related to fetal alcohol syndrome, a condition involving retinal degeneration, a disorder affecting learning and memory, or a neuropsychiatric disorder in a subject, by administering a therapeutically effective amount of a NAP-like peptide mimetic or SAL-like peptide mimetic with the formula listed above, to a subject in need of treatment, thereby treating or preventing the neurodegenerative disorder, the cognitive deficit, the autoimmune disorder, peripheral neurotoxicity, motor dysfunction, sensory dysfunction, anxiety, depression, schizophrenia, psychosis, the condition related to fetal alcohol syndrome, the condition involving retinal degeneration, the disorder affecting learning and memory, or the neuropsychiatric disorder in the subject. In a preferred embodiment, the administered NAP-like peptide mimetic or SAL-like peptide mimetic includes one of the following amino acid sequences: NATLSIHQ (SEQ ID NO:4) and STPTAIPQ (SEQ ID NO:6).

BRIEF DESCRIPTION OF THE DRAWINGS

FIG. 8: NAT treatment leads to a statistically significant increase in the amount of ADNP protein in cell nucleus.

DEFINITIONS

Figure 1:
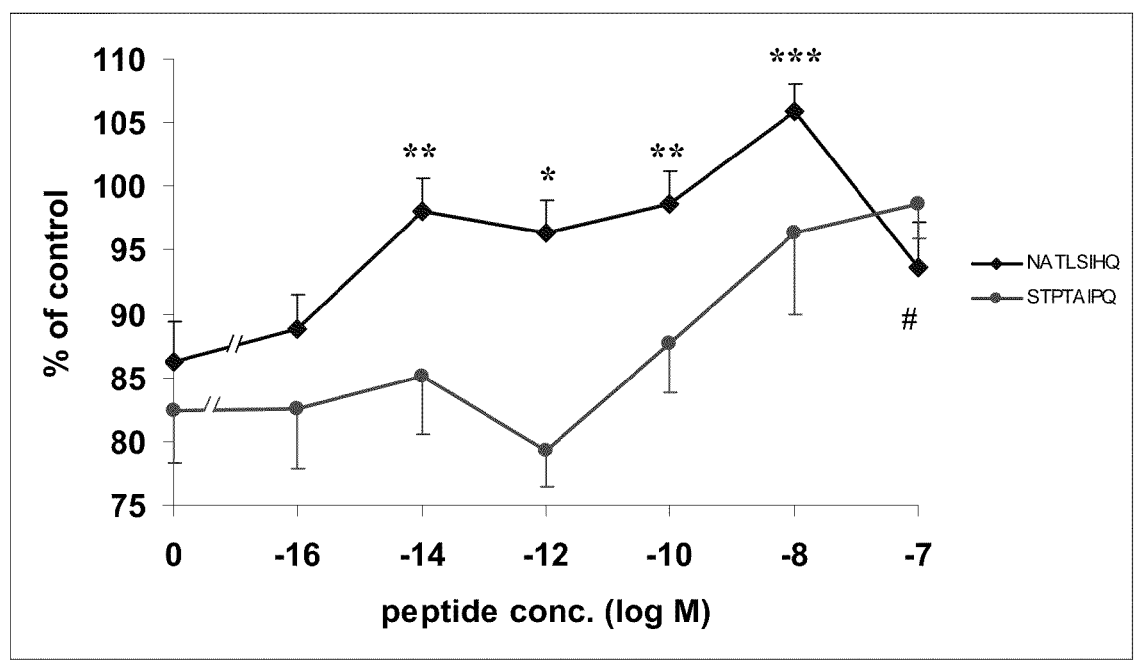
FIG. 1: The effect of peptides on survival of astrocytes following incubation with 200 mM $ZnCl_2$ for 4 hrs. The graph depicts at least 3 experiments per peptide which were each performed in quintuplets. NATLSIHQ (SEQ ID NO:4): *=p<0.05; =p<0.005, *=p<0.0005; STPTAIPQ (SEQ ID NO:6): #=p<0.05 (In comparison to the negative control—no additions).

The phrases "NAP-like peptide mimetics" and "NAP-like peptides" refer equally to both peptides and mimetics that have similarity to NAP (NAPVSIPQ) (SEQ ID NO:1). The phrases therefore refer to peptides and mimetics comprising a sequence having the following formula: $(R^1)_a$—$(R^2)$—$(R^3)_b$, where $R^1$ and $R^3$ are independently selected and are amino acid sequences comprising from 1 to about 40 amino acids wherein each amino acid is independently selected from the group consisting of naturally occurring amino acids and amino acid analogs; $R^2$ is a NAP-like peptide such as: NAVLSIHQ (SEQ ID NO:2), NATLSVHQ (SEQ ID NO:3), NATLSIHQ (SEQ ID NO:4), NATLSIVHQ (SEQ ID NO:5), STPTAIPQ (SEQ ID NO:6), NTPVSIPQ (SEQ ID NO:7), APVSIPQ (SEQ ID NO:8), NTPISIPQ (SEQ ID NO:9), NAPVSIP (SEQ ID NO:10), NAPVAVPQ (SEQ ID NO:11), NARVSIPQ (SEQ ID NO:12), DAPVSVPQ (SEQ ID NO:13), NXPVSIPQ (SEQ ID NO:14), NXP+SIPQ (SEQ ID NO:15), NAPV++PQ (SEQ ID NO:16), NAXVSIPQ (SEQ ID NO:17) and +APVS+PQ (SEQ ID NO:18), wherein X refers to any amino acid and + refers to a conservative amino acid; and a and b are independently selected and are equal to zero or one, with the proviso that the NAP-like peptide mimetic is not NAP. The phrase also refers to D-amino acid analogs, for example where as few as one or as many as all amino acids are in the D configuration.

The phrases "SAL-like peptide mimetics" and "SAL-like peptides" refer equally to both peptides and mimetics that have similarity to SAL (SALLRSIPA) (SEQ ID NO:19). The phrases therefore refer to peptides comprising a sequence having the following formula: $(R^1)_a$—$(R^2)$—$(R^3)_b$, where $R^1$ and $R^3$ are independently selected and are amino acid sequences comprising from 1 to about 40 amino acids wherein each amino acid is independently selected from the group consisting of naturally occurring amino acids and amino acid analogs; $R^2$ is a SAL-like peptide such as: ALLRSIPA (SEQ ID NO:20), ALLRSIP (SEQ ID NO:21), AMLRSIPA (SEQ ID NO:22), ALLRAIPA (SEQ ID NO:23), SALLRSIP (SEQ ID NO:24), SALLRAIP (SEQ ID NO:25), ALLRTIPA (SEQ ID NO:26), ALLRSVPA (SEQ ID NO:27), A+LRSIPA (SEQ ID NO:28), ALLR+IPA (SEQ ID NO:29), SALLR+IP (SEQ ID NO:30), and ALLRS+PA (SEQ ID NO:31) wherein X refers to any amino acid and + refers to a conservative amino acid; and a and b are independently selected and are equal to zero or one, with the proviso that the SAL-like peptide mimetic is not SAL. The phrase also refers to D-amino acid analogs, for example where as few as one or as many as all amino acids are in the D configuration.

The phrase "ADNF polypeptide" refers to one or more activity dependent neurotrophic factors (ADNF) that have an active core site comprising the amino acid sequence of NTPVSIPQ (SEQ ID NO:1) (referred to as "NAP") or SALLRSIPA (SEQ ID NO:19) (referred to as "SAL") and that have neurotrophic/neuroprotective activity as measured with in vitro cortical neuron culture assays described by, e.g., Hill et al., *Brain Res.* 603:222-233 (1993); Brenneman & Gozes, *J. Clin. Invest.* 97:2299-2307 (1996); and Forsythe & Westbrook, *J. Physiol. Lond.* 396:515 (1988). An ADNF polypeptide can be an ADNF I polypeptide, an ADNF III polypeptide, their alleles, polymorphic variants, analogs, interspecies homolog, any subsequences thereof (e.g., SALLRSIPA (SEQ ID NO:19) or NAPVSIPQ (SEQ ID NO:1)) or lipophilic variants that exhibit neuroprotective/neurotrophic action on, e.g., neurons originating in the central nervous system either in vitro or in vivo. An "ADNF polypeptide" can also refer to a mixture of an ADNF I polypeptide and an ADNF III polypeptide.

The phrase "ADNF III polypeptide" or "ADNF III," also called activity-dependent neuroprotective protein (ADNP), refers to one or more activity dependent neurotrophic factors (ADNF) that have an active core site comprising the amino acid sequence of NAPVSIPQ (SEQ ID NO:1) (referred to as "NAP") and that have neurotrophic/neuroprotective activity as measured with in vitro cortical neuron culture assays described by, e.g., Hill et al., Brain Res. 603, 222-233 (1993); and Gozes et al., Proc. Natl. Acad. Sci. USA 93, 427-432 (1996). An ADNF polypeptide can be an ADNF III polypeptide, allelelic or polymorphic variant, analog, interspecies homolog, or any subsequences thereof (e.g., NAPVSIPQ; SEQ ID NO:1) that exhibit neuroprotective/neurotrophic action on, e.g., neurons originating in the central nervous system either in vitro or in vivo. ADNF III polypeptides can range from about eight amino acids and can have, e.g., between 8-20, 8-50, 10-100 or about 1000 or more amino acids.

Full length human ADNF III has a predicted molecular weight of 123,562.8 Da (>1000 amino acid residues) and a theoretical pI of about 6.97. As described above, ADNF III polypeptides have an active site comprising an amino acid sequence of Asn-Ala-Pro-Val-Ser-Ile-Pro-Gln (SEQ ID NO:1) (also referred to as "NAPVSIPQ" or "NAP"). See Zamostiano et al., *J. Biol. Chem.* 276:708-714 (2001) and Bassan et al., *J. Neurochem.* 72:1283-1293 (1999). Unless indicated as otherwise, "NAP" refers to a peptide having an amino acid sequence of Asn-Ala-Pro-Val-Ser-Ile-Pro-Gln (SEQ ID NO:1), not a peptide having an amino acid sequence of Asn-Ala-Pro. Full-length amino acid and nucleic acid sequences of ADNF III can be found in International PCT Application Publication Nos. WO 98/35042, WO 00/27875, U.S. Pat. Nos. 6,613,740 and 6,649,411. The Accession number for the human sequence is NP_852107, see also Zamostiano et al., supra.

The term "ADNF I" refers to an activity dependent neurotrophic factor polypeptide having a molecular weight of about 14,000 Daltons with a pI of 8.3±0.25. As described above, ADNF I polypeptides have an active site comprising an amino acid sequence of Ser-Ala-Leu-Leu-Arg-Ser-Ile-Pro-Ala (SEQ ID NO:19) (also referred to as "SALLRSIPA" or "SAL" or "ADNF-9"). See Brenneman & Gozes, *J. Clin. Invest.* 97:2299-2307(1996), Glazner et al., *Anat. Embryol.* ((Berl). 200:65-71(1999), Brenneman et al., *J. Pharm. Exp. Ther.,* 285:619-27 (1998), Gozes & Brenneman, *J. Mol. Neurosci.* 7:235-244(1996), and Gozes et al., *Dev. Brain Res.* 99:167-175(1997). Unless indicated as otherwise, "SAL" refers to a peptide having an amino acid sequence of Ser-Ala-Leu-Leu-Arg-Ser-Ile-Pro-Ala (SEQ ID NO:19), not a peptide having an amino acid sequence of Ser-Ala-Leu. A full length amino acid sequence of ADNF I can be found in International PCT Application Publication No. WO 96/11948.

The term "subject" refers to any mammal, in particular human, at any stage of life.

The term "contacting" is used herein interchangeably with the following: combined with, added to, mixed with, passed over, incubated with, flowed over, etc. Moreover, the polypeptides or nucleic acids of the present invention can be "administered" by any conventional method such as, for example, parenteral, oral, topical, nasal, and inhalation routes. In some embodiments, parenteral and nasal or inhalation routes are employed.

The term "biologically active" refers to a peptide sequence that will interact with naturally occurring biological molecules to either activate or inhibit the function of those molecules in vitro or in vivo. The term "biologically active" is most commonly used herein to refer to NAP-like peptide mimetics that exhibit neuroprotective/neurotrophic action on neurons originating in the central nervous system both in vitro or in vivo. Thus, the present invention provides polypeptide subsequences that have the same or similar activity as NAP when tested, e.g., cerebral cortical cultures treated with a neurotoxin (see Gozes et al. *Proc. Nat'l. Acad. Sci. USA* 93:427-432 (1996)). The peptides can also be tested as described herein to determine their ability to compete with NAP-tubulin binding by at least 2-10%, preferably greater than 10%.

The phrase "neurodegenerative disorders or cognitive deficits" includes, but is not limited to the following conditions: diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity; diseases affecting sensory neurons such as Friedreich's ataxia, diabetes, peripheral neuropathy, and retinal neuronal degeneration; diseases of limbic and cortical systems such as cerebral amyloidosis, Pick's atrophy, and Retts syndrome; neurodegenerative pathologies involving multiple neuronal systems and/or brainstem including Alzheimer's disease, Parkinson's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration, ALS, corticobasal degeneration, and progressive supranuclear palsy; pathologies associated with developmental retardation and learning impairments, Down's syndrome, and oxidative stress induced neuronal death; pathologies arising with aging and chronic alcohol or drug abuse including, for example, (i) with alcoholism, the degeneration of neurons in locus coeruleus, cerebellum, cholinergic basal forebrain, (ii) with aging, degeneration of cerebellar neurons and cortical neurons leading to cognitive and motor impairments, and (iii) with chronic amphetamine abuse, degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia, closed head trauma, and direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor).

"Peripheral neurotoxicity" may be identified and diagnosed in a subject by a variety of techniques. Typically it may be measured by motor dysfunction, muscle wasting, or a change in sense of smell, vision or hearing, or changes in deep tendon reflexes, vibratory sense, cutaneous sensation, gait and balance, muscle strength, orthostatic blood pressure, and chronic or intermittent pain. In humans these symptoms are also sometimes demonstrative of toxic effects in both the PNS and the CNS. Ultimately, there are hundreds of possible peripheral neuropathies that may result from neurotoxicity. Reflecting the scope of PNS activity, symptoms may involve sensory, motor, or autonomic functions. They can be classified according to the type of affected nerves and how long symptoms have been developing. Peripheral neurotoxicity can be induced by chemotherapeutic agents (anti-cancer, anti-microbial and the like) and by disease processes. (See, e.g., U.S. patent application Ser. No. 11/388,634).

"Conditions involving retinal degeneration" include, but are not limited to, laser-induced retinal damage and ophthalmic diseases, such as glaucoma, Retinitis pigmentosa, Usher syndrome, artery or vein occlusion, diabetic retinopathy, retrolental fibroplasias or retinopathy of prematurity (R.L.F./R.O.P.), retinoschisis, lattic degeneration, and macular degeneration.

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder and attention deficit disorders) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV) (see also Benitez-King G. et al., Curr Drug Targets CNS Neurol Disord. 2004 December; 3(6):515-33. Review). Typically, such disorders have a complex genetic and/or a biochemical component.

A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., Diagnostic and Statistical Manual of Mental Disorders, Fourth Edition, (DSM IV).

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

"Anxiety," "anxiety disorder," and "anxiety-related disorder refer to psychiatric syndromes characterized by a subjective sense of unease, dread, or foreboding, e.g., panic disorder, generalized anxiety disorder, attention deficit disorder, attention deficit hyperactive disorder, obsessive-compulsive disorder, and stress disorders, e.g., acute and post-traumatic. Diagnostic criteria for these disorders are well known to those of skill in the art (see, e.g., *Harrison's Principles of Internal Medicine*, pp. 2486-2490 (Wilson et al., eds., 12th ed. 1991) and DSM IV).

An "autoimmune disorder" refers to an autoimmune disease such as multiple sclerosis, myasthenia gravis, Guillan-Barre syndrome (antiphospholipid syndrome), systemic lupus erytromatosis, Behcet's syndrome, Sjogrens syndrome, rheumatoid arthritis, Hashimoto's disease/hypothyroiditis, primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock (see, e.g., Schneider A. et al., *J Biol. Chem.* 279:55833-9 (2004)).

"Motor dysfunctions" include muscle wasting and changes in gait, balance, and muscle strength. "Sensory dysfunctions" may be measured by changes in sense of smell, vision or hearing, or changes in deep tendon reflexes, vibratory sense, cutaneous sensation, or chronic or intermittent pain. Sometimes sensory dysfunctions are associated with disease, and can be experienced as pain or pins-and-needles, burning, crawling, or prickling sensations, e.g., in the feet and lower legs. In humans, both motor and sensory dysfunctions indicate effects in both the PNS and the CNS which may be caused by chemical (e.g., chemotherapeutics) or disease states.

The terms "polypeptide," "peptide" and "protein" are used interchangeably herein to refer to a polymer of amino acid residues. Generally, a peptide refers to a short polypeptide. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in International PCT Application Publication No. WO 01/12654, which may improve oral availability and other drug like characteristics of the compound. In such embodiments, one or more, and potentially all of the amino acids of NAP-like or SAL-like peptide mimetics will have D-chirality. The therapeutic use of peptides can be enhanced by using D-amino acids to provide longer half life and duration of action. However, many receptors exhibit a strong preference for L-amino acids, but examples of D-peptides have been reported that have equivalent activity to the naturally occurring L-peptides, for example, pore-forming antibiotic peptides, beta amyloid peptide (no change in toxicity), and endogenous ligands for the CXCR4 receptor. In this regard, NAP-like or SAL-like peptide mimetics also retain activity in the D-amino acid form.

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g., Creighton, Proteins (1984)).

One of skill in the art will appreciate that many conservative variations of the nucleic acid and polypeptide sequences provided herein yield functionally identical products. For example, due to the degeneracy of the genetic code, "silent substitutions" (i.e., substitutions of a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties (see the definitions section), are also readily identified as being highly similar to a disclosed amino acid sequence, or to a disclosed nucleic acid sequence that encodes an amino acid.

In addition, certain protecting groups may be added to peptides according to the invention. The protecting group may be added to either the N-terminal or C-terminal end of the peptide, or both. As used herein, the term "protecting group" refers to a compound that renders a functional group unreactive, but is also removable so as to restore the functional group to its original state. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006. Examples of protecting groups include, but are not limited to: Fmoc (9-fluorenylmethyl carbamate, Boc, benzyloxy-carbonyl (Z), alloc (allyloxycarbonyl), and lithographic protecting groups.

The terms "isolated," "purified" or "biologically pure" refer to material that is substantially or essentially free from components that normally accompany it as found in its native state.

"An amount sufficient" or "an effective amount" or a "therapeutically effective amount" is that amount of a given NAP-like or SAL-like peptide mimetic that exhibits the activity of interest or which provides either a subjective relief of a symptom(s) or an objectively identifiable improvement as noted by the clinician or other qualified observer. In therapeutic applications, the NAP-like or SAL-like peptide mimetics of the invention are administered to a patient in an amount sufficient to reduce or eliminate symptoms. An amount adequate to accomplish this is defined as the "therapeutically effective dose." The dosing range varies with the NAP-like or SAL-like peptide mimetic used, the route of administration and the potency of the particular NAP-like or SAL-like peptide mimetic, and the presence or absence of additional therapeutic compounds in the pharmaceutical composition.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100% Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, less than about 2000 Daltons, between about 100 and about 1000 Daltons, or between about 200 and about 500 Daltons.

DETAILED DESCRIPTION OF THE INVENTION

I. Introduction

We have previously shown that NAP (NAPVSIPQ, SEQ ID NO:1) protects neurons and glial cells through interaction with brain tubulin (Divinski et al, *J. Biol. Chem.* 279, 28531-28538 (2004)) and stimulation of tubulin assembly to increase neurite outgrowth which is associated with microtubule assembly (Gozes and Spivak-Pohis, *Curr Alzheimer Res*, 3: 197-199 (2006)). By affinity chromatography, NAP was also shown to specifically interact with beta III tubulin (Divinski et al., *J. Neurochem*, 98, 973-984 (2006)). SAL has likewise been shown to confer neuroprotection (e.g., Gozes et al., 2000; Brenneman et al., 1998). Previously it had been thought that the eight amino acid NAP core sequence and the nine amino acid SAL core sequence could not be modified without loss of function. This application provides the first demonstration of peptides that have sequence similarities with the NAP and SAL core sequences, but that also have biological function, e.g., promotion of survival of neuronal cells. NAP-like and SAL-like peptide mimetics were identified and are listed in Table 1 and 2 herein. Biological activity was found in at least two of the NAP-like peptide mimetics or SAL-like peptide mimetics: NATLSIHQ (SEQ ID NO:4) and STPTAIPQ (SEQ ID NO:6). These compounds can be used as therapeutic molecules for treatment of neurodegenerative diseases or disorders.

II. Design and Synthesis of NAP-Like and SAL-Like Peptide Mimetics

Modifications of polypeptides and peptides comprising the core NAP-like or SAL-like peptide mimetic active site can be made, e.g., by systematically adding one amino acid at a time to the N or C-terminus of the active core site and screening the resulting peptide for biological activity, as described herein. In addition, the contributions made by the side chains of various amino acid residues in such peptides can be probed via a systematic scan with a specified amino acid, e.g., Ala. Polypeptides derived from the NAP-like or SAL-like peptide can also be made.

Peptides with NAP-like and SAL-like sequences and properties can be derived from known proteins with sequences found in, e.g., publicly-available databases. Examples include NCBI, OMIM, UniProtKB/Swiss-Prot, EMBOSS Pairwise Alignment Algorithms, ClustalW, Tcoffee, BLAST, RADAR, PROSITE, Phylogenetic Tree, and Selection.

NCBI (National Center for Biotechnology Information, USA) includes PubMed, a service of the U.S. National Library of Medicine that includes over 16 million citations from MEDLINE and other life science journals for biomedical articles back to the 1950s. PubMed includes links to full text articles and other related resources. NCBI also developed OMIM (Online Mendelian Inheritance in Man), a catalog of human genes and genetic disorders. OMIM contains textual information, references, links to MEDLINE and sequence records in the Entrez system, and links to additional related resources at NCBI and elsewhere.

UniProtKB/Swiss-Prot is a manually annotated protein knowledgebase which, together with UniProtKB/TrEMBL, its computer-annotated supplement, gives access to all the publicly available protein sequences. This database distinguishes itself from other protein sequence databases by three distinct criteria: integration with other databases, minimal redundancy and high annotation (such as; function of the protein, post-translational modification, domains and sites, secondary structure, quaternary structure, disease associated with deficiencies in the protein sequence, variants, etc).

EMBOSS is "The European Molecular Biology Open Software Suite". The EMBOSS Pairwise Alignment tool is used to compare 2 sequences. ClustalW is a general purpose multiple sequence alignment program for DNA or proteins. It produces biologically meaningful multiple sequence alignments of divergent sequences, calculates the best match for the selected sequences, and lines them up so that the identities, similarities and differences can be seen. T-coffee is another option similar to ClustalW.

Basic Local Alignment Search Tool (BLAST) finds regions of local similarity between sequences. The program compares nucleotide or protein sequences to sequence databases and calculates the statistical significance of matches. BLAST can be used to infer functional and evolutionary relationships between sequences as well as help identify members of gene families.

PROSITE is a database of protein families and domains that groups proteins on the basis of similarities in their sequences into a limited number of families. Proteins or protein domains belonging to a particular family generally share functional attributes and are derived from a common ancestor. PROSITE currently contains patterns and profiles specific for more than a thousand protein families or domains. Each of these signatures comes with documentation providing background information on the structure and function of these proteins.

Phylogenetic tree relies on the NJ (Neighbour Joining) method of Saitou and Nei, which first calculates distances (percent divergence) between all pairs of sequence from a multiple alignment and then applies the NJ method to the distance matrix. Selecton enables detecting of the selective forces at a single amino acid site. The ratio of non-synonymous (amino-acid altering) to synonymous (silent) substitutions, known as the Ka/Ks ratio, is used to estimate both positive and purifying selection at each amino acid site.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see Giliman & Smith, *Gene* 8:81-97 (1979); Roberts et al., *Nature* 328:731-734 (1987)).

Most commonly, polypeptide sequences are altered by changing the corresponding nucleic acid sequence and expressing the polypeptide. However, polypeptide sequences are also optionally generated synthetically using commercially available peptide synthesizers to produce any desired polypeptide (see Merrifield, *Am. Chem. Soc.* 85:2149-2154 (1963); Stewart & Young, *Solid Phase Peptide Synthesis* (2nd ed. 1984)).

One of skill can select a desired nucleic acid or polypeptide of the invention based upon the sequences provided and upon knowledge in the art regarding proteins generally. Knowledge regarding the nature of proteins and nucleic acids allows one of skill to select appropriate sequences with activity similar or equivalent to the nucleic acids and polypeptides disclosed herein. The definitions section, supra, describes exemplar conservative amino acid substitutions.

Polypeptides are evaluated by screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate are all assayed according to standard techniques. Here, polypeptides that comprise a NAP-like or SAL-like mimetic active site are evaluated for biological activity, e.g., reduction or inhibition of neuronal cell death.

More particularly, the small peptides of the present invention can be screened by employing suitable assays and animal models known to those skilled in the art.

Using these assays and models, one of ordinary skill in the art can screen a large number of NAP-like and SAL-like peptide mimetics in accordance with the teachings of the present invention for those that possess the desired activity.

The peptides of the invention may be prepared via a wide variety of well-known techniques. Peptides of relatively short size are typically synthesized on a solid support or in solution in accordance with conventional techniques (see, e.g., Merrifield, *Am. Chem. Soc.* 85:2149-2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the peptides of this invention. Techniques for solid phase synthesis are described by Barany & Merrifield, *Solid-Phase Peptide Synthesis*; pp. 3-284 in *The Peptides: Analysis, Synthesis, Biology*. Vol. 2: *Special Methods in Peptide Synthesis*, Part A.; Merrifield et al 1963; Stewart et al. 1984). NAP and related peptides are synthesized using standard Fmoc protocols (Wellings & Atherton, *Meth ods Enzymol.* 289:44-67 (1997)).

In addition to the foregoing techniques, the peptides for use in the invention may be prepared by recombinant DNA methodology. Generally, this involves creating a nucleic acid sequence that encodes the protein, placing the nucleic acid in an expression cassette under the control of a particular promoter, and expressing the protein in a host cell. Recombinantly engineered cells known to those of skill in the art include, but are not limited to, bacteria, yeast, plant, filamentous fungi, insect (especially employing baculoviral vectors) and mammalian cells.

The recombinant nucleic acids are operably linked to appropriate control sequences for expression in the selected host. For *E. coli*, example control sequences include the T7, trp, or lambda promoters, a ribosome binding site and, preferably, a transcription termination signal. For eukaryotic cells, the control sequences typically include a promoter and, preferably, an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods. Such methods include, for example, the calcium chloride transformation method for *E. coli* and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant peptides can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology* Vol. 182: Guide to Polypeptide Purification (1990)). Optional additional steps include isolating the expressed protein to a higher degree, and, if required, cleaving or otherwise modifying the peptide, including optionally renaturing the protein.

After chemical synthesis, biological expression or purification, the peptide(s) may possess a conformation substantially different than the native conformations of the constituent peptides. In this case, it is helpful to denature and reduce the peptide and then to cause the peptide to re-fold into the preferred conformation. Methods of reducing and denaturing peptides and inducing re-folding are well known to those of skill in the art (see Debinski et al., *J. Biol. Chem.* 268:14065-14070 (1993); Kreitman & Pastan, *Bioconjug. Chem.* 4:581-585 (1993); and Buchner et al., *Anal. Biochem.* 205:263-270 (1992)). Debinski et al., for example, describe the denaturation and reduction of inclusion body peptides in guanidine-DTE. The peptide is then refolded in a redox buffer containing oxidized glutathione and L-arginine.

One of skill will recognize that modifications can be made to the peptides without diminishing their biological activity. Some modifications may be made to facilitate the cloning, expression, or incorporation of the targeting molecule into a fusion peptide. Such modifications are well known to those of III. Functional Assays and Therapeutic Uses of NAP-Like and SAL-Like Peptide Mimetics One method to determine biological activity of a NAP-like or SAL-like peptide mimetic is to assay their ability to protect neuronal cells from death. One such assay is performed using dissociated cerebral cortical cultures prepared as described (Brenneman & Gozes, *J. Clin. Invest.* 97:2299-2307 (1996)). The test paradigm consists of the addition of a test peptide to cultures that are co-treated with tetrodotoxin (TTX). TTX produces an apoptotic death in these cultures and, thus, is used as a model substance to demonstrate efficacy against this "programmed cell death" and all other means that produce this type of death mechanism. The duration of the test period is 5 days, and neurons are counted and identified by characteristic morphology and by confirmation with an immunocytochemical marker for neurons: e.g., neuron specific enolase. Other cell based assays include assaying the ability of NAP-like or SAL-like peptides to promote survival of neuronal cells exposed to, e.g., beta-amyloid protein or high levels of $ZnCl_2$. These assays are demonstrated in Example 2, herein. Neuronal cell survival promoted by NAP-like and SAL-like proteins can also be measured in the presence of neurotoxins such as, gp120, the envelope protein from HIV and N-methyl-D-aspartic acid.

In another aspect, the present invention provides a method for reducing neuronal cell death, the method comprising contacting neuronal cells with a NAP-like or SAL-like peptide mimetic in an amount sufficient to reduce neuronal cell death. In a further aspect, the NAP-like or SAL-like peptide mimetic comprises at least one D-amino acid within its active core site, preferably at the N-terminus and/or the C-terminus of the active core site. In another preferred aspect, each amino acid of the core NAP-like or SAL-like peptide is a D-amino acid. Preferred NAP-like or SAL-like peptide mimetics, include, e.g., NATLSIHQ (SEQ ID NO:4) and STPTAIPQ (SEQ ID NO:6).

NAP-like and SAL-like peptide mimetics of the present invention can be used in the treatment of neurological disorders and for the prevention of neuronal cell death. For example, NAP-like peptide mimetics of the present invention can be used to prevent the death of neuronal cells including, but not limited to, spinal cord neurons, hippocampal neurons, cerebral cortical neurons and cholinergic neurons. More particularly, NAP-like and SAL-like peptide mimetics of the present invention can be used in the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease. Preferred NAP-like or SAL-like peptide mimetics, include, e.g., NATLSIHQ (SEQ ID NO:4) and STPTAIPQ (SEQ ID NO:6).

As such, the NAP-like and SAL-like peptide mimetics of the present invention can be used to reduce gp120-induced neuronal cell death by administering an effective amount of an NAP-like peptide mimetic of the present invention to a patient infected with the HIV virus. The NAP-like and SAL-like peptide mimetics of the present invention can also be used to reduce neuronal cell death associated with excito-toxicity induced by N-methyl-D-aspartate stimulation, the method comprising contacting neuronal cells with an NAP-like and SAL-like peptide mimetic of the present invention in an amount sufficient to prevent neuronal cell death. The NAP-like and SAL-like peptide mimetics of the present invention can also be used to reduce cell death induced by the β-amyloid peptide in a patient afflicted or impaired with Alzheimer's disease, the method comprising administering to the patient an NAP-like and SAL-like peptide mimetic of the present invention in an amount sufficient to prevent neuronal cell death. The NAP-like and SAL-like peptide mimetics can also be used to alleviate learning impairment produced by cholinergic blockage in a patient afflicted or impaired with Alzheimer's disease. For example, NAP-like and SAL-like peptide mimetics can be used to improve short-term and/or reference memory in Alzheimer's patients. Preferred NAP-like or SAL-like peptide mimetics, include, e.g., NATLSIHQ (SEQ ID NO:4) and STPTAIPQ (SEQ ID NO:6).

Similarly, it is apparent to those of skill in the art that the NAP-like and SAL-like peptide mimetics of the present invention can be used in a similar manner to prevent neuronal cell death associated with a number of other neurological diseases and deficiencies. Pathologies that would benefit from therapeutic and diagnostic applications of this invention include conditions (diseases and insults) leading to neuronal cell death and/or sub-lethal neuronal pathology including, for example, the following: diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity; diseases affecting sensory neurons such as Friedreich's ataxia, diabetes, peripheral neuropathy, retinal neuronal degeneration; diseases of limbic and cortical systems such as cerebral amyloidosis, Pick's atrophy, Retts syndrome; neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration; pathologies associated with developmental retardation and learning impairments, and Down's syndrome, and oxidative stress induced neuronal death; pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia, closed head trauma, or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor, peripheral neuropathies resulting from, e.g., chemotherapy treatments, and retinal damage from laser eye treatments). NAP-like and SAL-like peptide mimetics of the present invention can also be used to treat autoimmune diseases, such as multiple sclerosis and mental disorders, such as schizophrenia and depression. Preferred NAP-like or SAL-like peptide mimetics, include, e.g., NATLSIHQ (SEQ ID NO:4) and STPTAIPQ (SEQ ID NO:6).

Thus, the NAP-like and SAL-like peptide mimetics that reduce neuronal cell death can be screened using the various methods described in International PCT Application Publication No. WO98/35042, filed Feb. 7, 1997, and U.S. Pat. No. 6,613,740, filed Nov. 6, 1998. For example, it will be readily apparent to those skilled in the art that using the teachings set forth above with respect to the design and synthesis of NAP-like and SAL-like peptide mimetics and the assays described herein, one of ordinary skill in the art can identify other biologically active NAP-like peptide mimetics comprising at least one D-amino acid within their active core sites. For example, Brenneman et al., *Nature* 335:639-642 (1988), and Dibbern et al., *J. Clin. Invest.* 99:2837-2841 (1997), teach assays that can be used to screen ADNF polypeptides that are capable of reducing neuronal cell death associated with envelope protein (gp120) from HIV. Also, Brenneman et al., *Dev. Brain Res.* 51:63-68 (1990), and Brenneman & Gozes, *J. Clin. Invest.* 97:2299-2307 (1996), teach assays that can be used to screen NAP-like and SAL-like peptide mimetics which are capable of reducing neuronal cell death associated with excito-toxicity induced by stimulation by N-methyl-D-aspartate. Other assays described in, e.g., International PCT Application Publication No. WO98/35042 can also be used to identify other biologically active NAP-like and SAL-like peptide mimetics.

Moreover, NAP-like and SAL-like peptide mimetics that reduce neuronal cell death can be screened in vivo. For example, the ability of NAP-like and SAL-like peptide mimetics that can protect against learning and memory deficiencies associated with cholinergic blockade can be tested. For example, cholinergic blockade can be obtained in rats by administration of the cholinotoxin AF64A, and ADNF polypeptides can be administered intranasally and the water maze experiments can be performed (Gozes et al., *Proc. Natl. Acad. Sci. USA* 93:427-432 (1996)). Animals treated with efficacious NAP-like peptide mimetics would show improvement in their learning and memory capacities compared to the control.

Furthermore, the ability of NAP-like and SAL-like peptide mimetics that can protect or reduce neuronal cell death associated with Alzheimer's disease can be screened in vivo. For these experiments, apolipoprotein E (ApoE)-deficient homozygous mice can be used (Plump et al., *Cell* 71:343-353 (1992); Gordon et al., *Neuroscience Letters* 199:1-4 (1995); Gozes et al., *J. Neurobiol.* 33:329-342 (1997)).

The ability of NAP-like and SAL-like peptide mimetics to inhibit immune cell proliferation, can be assayed as described in Offen et al. *J Mol. Neurosci.* 15(3):167-76 (2000) and International PCT Application Publication No. WO04/060309, both of which describe the MOG-induced chronic EAE mouse model and are herein incorporated by reference for all purposes. The STOP protein-deficient mouse is an art accepted model of schizophrenia can be used to assess antischizophrenia activity of NAP-like and SAL-like peptide mimetics. See, e.g., Andrieux et al., *Genes & Develop.,* 16:2350-2364 (2002), which is herein incorporated by reference for all purposes. Anti-anxiety activity of NAP-like and SAL-like peptide mimetics can be assessed using a mouse model and the Morris water maze paradigm, disclosed at International PCT Application Publication No. WO04/080957, which is herein incorporated by reference for all purposes. Reduction of peripheral neurotoxicity by NAP-like and SAL-like peptide mimetics can be assessed using a rat model and rota-rod and plantar tests. See, e.g., International PCT Application Publication No. WO06/099739, which is herein incorporated by reference for all purposes.

IV. Drug Discovery

The identification of tubulin as a NAP-interacting protein and the discovery of NAP-like sequences in tubulin allows the use of tubulin and tubulin-derived peptides as targets for further drug discovery, e.g., for the treatment of neuronal disorders such as neurodegenerative disorders (e.g., Alzheimer's disease, AIDS-related dementia, Huntington's disease, and Parkinson's disease), cognitive deficits, peripheral neurotoxicity, motor dysfunctions, sensory dysfunctions, anxiety, depression, psychosis, conditions involving retinal degeneration, disorders affecting learning and memory, or neuropsychiatric disorders, diseases related to neuronal cell death and oxidative stress, HIV-related dementia complex, stroke, head trauma, cerebral palsy, conditions associated with fetal alcohol syndrome, and autoimmune diseases, such as multiple sclerosis. Such therapeutics can also be used in methods of enhancing learning and memory both pre- and post-natally. Experiments can be carried out to find agents that bind the same site as NAP using the intact tubulin structure and NAP as a displacing agent (e.g., as described Katchalski-Katzir et al., *Biophys Chem.* 100(1-3):293-305 (2003); Chang et al., *J Comput Chem.* 24(16):1987-98 (2003)).

Preliminary screens can be conducted by screening for agents capable of binding to a polypeptide of the invention or tubulin, as at least some of the agents so identified are likely modulators binding activity. The binding assays usually involve contacting a polypeptide of the invention with one or more test agents and allowing sufficient time for the protein and test agents to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet and Yamamura, *Neurotransmitter, Hormone or Drug Receptor Binding Methods*, in *Neurotransmitter Receptor Binding* (Yamamura et al., eds.), pp. 61-89 (1985). The protein utilized in such assays can be naturally expressed, cloned or synthesized.

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if expression or activity of a polynucleotide or polypeptide of the invention is in fact upregulated. The animal models utilized in validation studies generally are mammals of any kind Specific examples of suitable animals include, but are not limited to, primates, mice, and rats.

The agents tested as modulators of the polypeptides of the invention can be any small chemical compound, or a biological entity, such as a protein, sugar, nucleic acid, RNAi, or lipid. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St.

Louis, Mo.), Fluka Chemika-Biochemica Analytika (Buchs, Switzerland) and the like. Modulators also include agents designed to reduce the level of mRNA of the invention (e.g. antisense molecules, ribozymes, DNAzymes and the like) or the level of translation from an mRNA.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity, e.g., tubulin binding. The compounds thus identified can serve as conventional "lead compounds" or can themselves be used as potential or actual therapeutics. Libraries available for screening for small active molecules include the Available Chemical Directory (ACD, 278,000 compounds), ACD screening library (>1,000,000 compounds), CRC Combined Chemical Dictionary (~350,000 compounds) Anisex (115,000 compounds) Maybridge (62,000 compounds) Derwent and NCI libraries.

V. Assays for Activity of Discovered Compounds

Additional drug discovery methods include screening for neuroprotective activity. Such activity can be tested in classical tissue culture models of neuronal stress and survival as described, e.g., in Divinski et al. (2006) and Gozes et al. (2005). These assays are known in the art and focus on the effect of test compounds on microtubule reorganization, neurite outgrowth, and protection from toxic factors.

In vivo assays to test neuroprotection in animal models are also known in the art. Tests that measure effects of various test substances on motor activity include the rotorod test, e.g., in rats. Olfaction capacity can be used to measure the effect of test substances on sensory activity. Such assays are described, e.g., in U.S. App. Publication No. 2006/0247168.

A well-established model for fetal alcohol syndrome can be used to test the efficacy of test compounds (Webster et al., *Neurobehav. Toxicol* 2:227-234 (1980)). This paradigm is a test for efficacy against severe oxidative stress produced from alcohol administration (Spong et al., 2001). This model allows for a rapid and relevant evaluation of agents efficacious against severe oxidative stress as well as fetal alcohol syndrome. To assess the protective effects of a test compound, the number of fetal demises can be determined.

Experiments to test the protective effect of a test compound on retinal cells exposed to lasers, e.g., in conditions of laser surgery, are described in U.S. Prov. App. No. 60,776,329. In brief, rats were exposed to laser photocoagulation and immediately treated either systemically or intravitreously with a protective compound. The animals were sacrificed and retinal tissue sections were observed for histological and morphological abnormalities.

As discussed above, modulators of NAP-like and SAL-like peptide mimetics can be assayed for ability to inhibit immune cell proliferation, anti-schizophrenia activity, anti-anxiety activity, and ability to reduce peripheral neurotoxicity VI. Pharmaceutical Administration The invention provides a number of neuroprotective NAP-like and SAL-like peptide mimetics and compositions for pharmaceutical administration. For example, a pharmaceutical composition can comprise one of the NAP-like or SAL-like peptide mimetics described herein, or more than one, in combination. Preferred NAP-like or SAL-like peptide mimetics, include, e.g., NATLSIHQ (SEQ ID NO:4) and STPTAIPQ (SEQ ID NO:6). The pharmaceutical composition can include additional neuroprotective compounds, such as ADNF polypeptides, in combination with the NAP-like or SAL-like peptide mimetic. Neuroprotective ADNF polypeptides include those comprising NAP (SEQ ID NO:1) or SAL (SEQ ID NO:19). The NAP-like peptide mimetic can comprise at least one D-amino acid, and as many as all of the amino acids can be D-chirality. In some embodiments, the additional neuroprotective peptide has at least one, and as many as all, D-amino acids.

The pharmaceutical compositions of the present invention are suitable for use in a variety of drug delivery systems. Peptides that have the ability to cross the blood brain barrier can be administered, e.g., systemically, nasally, etc., using methods known to those of skill in the art. Larger peptides that do not have the ability to cross the blood brain barrier can be administered to the mammalian brain via intracerebroventricular (ICV) injection or via a cannula using techniques well known to those of skill in the art (see, e.g., Motta & Martini, *Proc. Soc. Exp. Biol. Med.* 168:62-64 (1981); Peterson et al., *Biochem. Pharamacol.* 31:2807-2810 (1982); Rzepczynski et al., *Metab. Brain Dis.* 3:211-216 (1988); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neurol.* 125:72-81 (1994); Nikkhah et al., *Neuroscience* 63:57-72 (1994); Anderson et al., *J. Comp. Neurol.* 357:296-317 (1995); and Brecknell & Fawcett, *Exp. Neurol.* 138:338-344 (1996)).

Suitable formulations for use in the present invention are found in Remington's *Pharmaceutical Sciences* (17th ed. 1985)). In addition, for a brief review of methods for drug delivery, see Langer, *Science* 249:1527-1533 (1990). Suitable dose ranges are described in the examples provided herein, as well as in International PCT Application Publication No. WO 9611948.

As such, the present invention provides for therapeutic compositions or medicaments comprising one or more of the polypeptides described hereinabove in combination with a pharmaceutically acceptable excipient, wherein the amount of polypeptide is sufficient to provide a therapeutic effect.

In a therapeutic application, the polypeptides of the present invention are embodied in pharmaceutical compositions intended for administration by any effective means, including parenteral, topical, oral, nasal, pulmonary (e.g. by inhalation), systemic, or local administration. For parenteral administration, the pharmaceutical compositions are administered e.g., intravenously, subcutaneously, intradermally, or intramuscularly. Nasal pumps, topical patches, and eye drops can also be used.

Thus, the invention provides compositions for parenteral administration that comprise a solution of polypeptide, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like.

For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., *J Mol Neurosci.* 19(1-2):167-70 (2002)).

In therapeutic applications, the polypeptides of the invention are administered to a patient in an amount sufficient to reduce or eliminate symptoms of neurodegenerative disorders, cognitive deficits, and other conditions, or to enhance learning and memory. An amount adequate to accomplish this is defined as "therapeutically effective dose." Amounts effective for this use will depend on, for example, the particular polypeptide employed, the type of disease or disorder to be prevented, the manner of administration, the weight and general state of health of the patient, and the judgment of the prescribing physician.

For example, an amount of polypeptide falling within the range of a 100 ng to 10 mg dose given intranasally once a day (e.g., in the evening) would be a therapeutically effective amount. Alternatively, dosages may be outside of this range, or on a different schedule. For example, dosages may range from 0.0001 mg/kg to 10,000 mg/kg, and will preferably be about 0.001 mg/kg, 0.1 mg/kg, 1 mg/kg, 5 mg/kg, 50 mg/kg or 500 mg/kg per dose. Doses may be administered hourly, every 4, 6 or 12 hours, with meals, daily, every 2, 3, 4, 5, 6, or 7 days, weekly, every 2, 3, 4 weeks, monthly or every 2, 3 or 4 months, or any combination thereof. The duration of dosing may be single (acute) dosing, or over the course of days, weeks, months, or years, depending on the condition to be treated. Those skilled in the art can determine the suitable dosage, and may rely on preliminary data reported in Gozes et al., 2000; Gozes et al., 2002; Bassan et al. 1999; Zemlyak et al., *Regul. Pept.* 96:39-43 (2000); Brenneman et al., *Biochem. Soc. Trans.* 28: 452-455 (2000); *Erratum Biochem Soc. Trans.* 28:983; Wilkemeyer et al. *Proc. Natl. Acad. Sci. USA* 100: 8543-8548 (2003); Alcalay et al., *Neurosci Lett.* 361:128-31 (2004); and Gozes et al., *CNS Drug Rev.,* 11(4):353-68 (2005).

EXAMPLES

Example 1

Search for NAP-Like and SAL-Like Sequences

A bio-informatics search was launched to address whether there are NAP-like or SAL-like sequences in other proteins that provide neuroprotection (e.g., through interaction with microtubules) and whether there are tubulin specific sequences that resemble NAP and provide neuroprotection.

The NAP and SAL sequences were submitted to a number of different search engines: NCBI, OMIM, UniProtKB/Swiss-Prot, EMBOSS Pairwise Alignment Algorithms, ClustalW, T-coffee, BLAST, RADAR, PPSearch, PROSITE, Phylogenetic Tree, and Selecton.

In the search for human tubulin proteins, the field descriptions tubulin and the boolean operators for *Homo sapiens* organism were used in UniProtKB/Swiss-Prot. Blosum62 with water alignment was used in EMBOSS in order to find the best region of similarity between two sequences. Multiple alignments were obtained from ClustalW, with further use of the Jalview editor.

For BLAST, and the similar programs RADAR and PPSearch, human beta3 tubulin and its orthologs were used as a query. For Selecton, the CDS of tubulin and the 12 ortholog organisms were submitted in FASTA format as an input file.

The results are summarized below and in Table 1. Structural elements within tubulin that are important for protein-protein interaction and GTP binding show significant homology to NAP:

```
NAVLSIHQ    (SEQ ID NO: 2)    Tubulin beta 1

NAILSVHQ    (SEQ ID NO: 3)    Tubulin beta 2

NAILSIHQ    (SEQ ID NO: 4)    Tubulin beta 3
```

NCBI protein Access Numbers for the various tubulin subunits:

| | |
|---|---|
| Tubulin beta 1 | Q9H4B7 |
| Tubulin beta 2a | Q13885 |
| Tubulin beta 2b | Q9BVA1 |
| Tubulin beta 2c | P68371 |
| Tubulin beta 3 | Q13509 |
| Tubulin beta 4 | P04350 |
| Tubulin beta 5 | P07437 |
| Tubulin beta 6 | Q9BUF5 |

The sequence s NAVLSIHQ (SEQ ID NO:2), NATLSVHQ (SEQ ID NO:3), and NATLSIHQ (SEQ ID NO:4), found in tubulin beta1, beta2, and beta3, respectively, but not alpha tubulin. The sequence runs from amino acids 184-191. This sequence overlaps with an area that is hypothesized to be important in the longitudinal contacts between beta and alpha tubulin within a microtubule, i.e., it sits at a relatively exposed area at the top of the molecule which becomes hidden upon dimerization. The sequence is also close to the GTP binding pocket of beta-tubulin, particularly the area associated with ribose binding (Nogales and Wang (2006) *Curr Opin Cell Biol,* 18, 179-184; Nogales and Wang (2006) *Curr Opin Struct Biol,* 16, 221-229.

The homology is >50% but there is no preservation of the two prolines found in NAP. Given that prolines are often associated with protein-protein interactions, it is likely that NAPVSIPQ (SEQ ID NO:1) has additional protein binding or protein interaction/disruption activities while still having some intrinsic association with microtubules.

Other sequences with increased homology to NAPVSIPQ (SEQ ID NO:1) include STPTAIPQ (SEQ ID NO:6) (accession number Q7KZS6), which includes both a tubulin segment and a segment relating to a G-protein coupled receptor from the rhodopsin family. The latter has similarity to melanocortin 1 receptor associated with pigmentation.

Additional sequence similarities were observed with key proteins such as: citrate lyase (Table 1). ATP citrate-lyase is the primary enzyme responsible for the synthesis of cytosolic acetyl-CoA in many tissues. It has a central role in de novo lipid synthesis. In nervous tissue it may be involved in the biosynthesis of acetylcholine (by similarity).

TABLE 1

NAP (NAP VSIPQ) sequence homologies

```
Query    1 NAPVSIPQ   8 (SEQ ID NO: 1) DNA primase Acidovorax sp. JS42
             NXPVSIPQ    (SEQ ID NO: 14)
Sbjct    3 NTPVSIPQ  10 (SEQ ID NO: 7)

Query    2 APVSIPQ    8 (SEQ ID NO: 8) citrate lyase, alpha subunit Thermosinus
             APVSIPQ     (SEQ ID NO: 8) carboxydivorans Nor 1
Sbjct  217 APVSIPQ  223 (SEQ ID NO: 8)

Query    1 NAPVSIPQ   8 (SEQ ID NO: 1) putative citrate lyase alpha subunit
             NXP+SIPQ    (SEQ ID NO: 15) Streptococcus pyogenes
Sbjct  215 NTPISIPQ 222 (SEQ ID NO: 9) str. Manfredo Query    1 NAPVSIPQ   8 (SEQ ID NO: 1) citrate lyase alpha subunit Lactobacillus
             NXP+SIPQ    (SEQ ID NO: 15) paracasei
Sbjct  158 NTPISIPQ 165 (SEQ ID NO: 9)

Query    1 NAPVSIPQ   8 (SEQ ID NO: 1) Chain A, Crystal Structure Of The Puta-
                                         tive
             NXP+SIPQ    (SEQ ID NO: 15)         Alfa Subunit Of Citrate
Sbjct  215 NTPISIPQ 222 (SEQ ID NO: 9) Chain B, Crystal Structure Of The Puta-
                                         tive
                                         Alfa Subunit Of Citrate
                                         Lyase In Complex With Citrate From
                                         Streptococcus Mutans,
                                         Northeast Structural Genomic-
                                         s Target Smr12
                                         (Casp Target)

Query    1 NAPVSIPQ   8 (SEQ ID NO: 1) Citrate lyase alpha chain/Citrate CoA-
             NXP+SIPQ    (SEQ ID NO: 15) transferase Streptococcus
Sbjct  215 NTPISIPQ 222 (SEQ ID NO: 9) pyogenes MGAS10270]

Query    1 NAPVSIPQ   8 (SEQ ID NO: 1) citrate lyase alpha subunit Enterococcus
             NXP+SIPQ    (SEQ ID NO: 15) faecalis
Sbjct  215 NTPISIPQ 222 (SEQ ID NO: 9)

Query    1 NAPVSIP    7 (SEQ ID NO: 10) RING finger domain protein Neosartorya
             NAPVSIP     (SEQ ID NO: 10) fischeri NRRL 181
Sbjct  102 NAPYSIP  108 (SEQ ID NO: 10)

Query    2 APVSIPQ    8 (SEQ ID NO: 8) linear gramicidin synthetase subunit D
             APVSIPQ     (SEQ ID NO: 8) Mycobacterium avium 104
Sbjct  453 APVSIPQ  459 (SEQ ID NO: 8)

Query    2 APVSIPQ    8 (SEQ ID NO: 8) PstA Mycobacterium avium
             APVSIPQ     (SEQ ID NO: 8)
Sbjct  453 APVSIPQ  459 (SEQ ID NO: 8)

Query    2 APVSIPQ    8 (SEQ ID NO: 8) PstA Mycobacterium avium subsp.
             APVSIPQ     (SEQ ID NO: 8) paratuberculosis K-10
Sbjct  461 APVSIPQ  467 (SEQ ID NO: 8)

Query    1 NAPVSIPQ   8 (SEQ ID NO: 1) glucose repression mediator pro-
                                         tein Pichia
             NAPV++PQ    (SEQ ID NO: 16) stipitis CBS 6054
Sbjct  760 NAPVAVPQ 767 (SEQ ID NO: 11)

Query    1 NAPVSIPQ   8 (SEQ ID NO: 1) adhesin family protein Granulibacter
             NAXVSIPQ    (SEQ ID NO: 17) bethesdensis CGDNIH1
Sbjct   73 NARVSIPQ  80 (SEQ ID NO: 12)

Query    1 NAPVSIPQ   8 (SEQ ID NO: 1) cation efflux family protein Pseudomonas
             +APVS+PQ    (SEQ ID NO: 18) fluorescens Pf-5
Sbjct  314 DAPVSVPQ 321 (SEQ ID NO: 13)
```

TABLE 2

SAL (SALLRSIPA) sequence homologies

```
Query    2 ALLRSIPA   9 (SEQ ID NO: 20) phosphatidylinositol glycan, class G,
             ALLRSIPA    (SEQ ID NO: 20) Daniorerio
Sbjct  614 ALLRSIPA 621 (SEQ ID NO: 20)
```

TABLE 2-continued

SAL (SALLRSIPA) sequence homologies

```
Query     2 ALLRSIPA   9 (SEQ ID NO: 20) heat shock protein 60 Salmo salar
            ALLRSIPA     (SEQ ID NO: 20)
Sbjct    53 ALLRSIPA  60 (SEQ ID NO: 20)

Query     2 ALLRSIP    8 (SEQ ID NO: 21) oligopeptide/dipeptide ABC transporter,
            ALLRSIP      (SEQ ID NO: 21) ATPase subunit Thermotoga petrophila
Sbjct   259 ALLRSIP  265 (SEQ ID NO: 21) RKU-1

Query     2 ALLRSIPA   9 (SEQ ID NO: 20) oligopeptide/dipeptide ABC transporter,
            A+LRSIPA     (SEQ ID NO: 28) ATPase subunit Burkholderia phymatum
Sbjct   346 AMLRSIPA 353 (SEQ ID NO: 22) STM815

Query     2 ALLRSIPA   9 (SEQ ID NO: 20) oligopeptide/dipeptide ABC transporter,
            ALLR+IPA     (SEQ ID NO: 29) ATPase subunit Burkholderia phymatum
Sbjct   254 ALLRAIPA 261 (SEQ ID NO: 23) STM815

Query     2 ALLRSIP    8 (SEQ ID NO: 21) ABC peptide transporter, ATP-binding
            ALLRSIP      (SEQ ID NO: 21) component Rhodococcus sp. RHA1
Sbjct   272 ALLRSIP  278 (SEQ ID NO: 21)

Query     1 SALLRSIP   8 (SEQ ID NO: 24) similar to ATPase, H+ transporting, V1
            SALLR+IP     (SEQ ID NO: 30) subunit E-
                                          like 2 isoform 2 Rattus norvegicus
Sbjct   124 SALLRAIP 131 (SEQ ID NO: 25)

Query     2 ALLRSIPA   9 (SEQ ID NO: 20) glucose inhibited division protein A
            A+LRSIPA     (SEQ ID NO: 28) Roseiflexus castenholzii
Sbjct   366 AMLRSIPA 373 (SEQ ID NO: 22) DSM 13941

Query     2 ALLRSIPA   9 (SEQ ID NO: 20) glucose inhibited division protein A
            A+LRSIPA     (SEQ ID NO: 28) Chloroflexus aggregans DSM 9485
Sbjct   346 AMLRSIPA 353 (SEQ ID NO: 22)

Query     2 ALLRSIPA   9 (SEQ ID NO: 20) glucose inhibited division protein A
            A+LRSIPA     (SEQ ID NO: 28) Herpetosiphon aurantiacus
Sbjct   346 AMLRSIPA 353 (SEQ ID NO: 22) ATCC 23779

Query     2 ALLRSIPA   9 (SEQ ID NO: 20) Glucose-inhibited division protein A
            A+LRSIPA     (SEQ ID NO: 28) Roseiflexus sp. RS-1
Sbjct   364 AMLRSIPA 371 (SEQ ID NO: 22) Length = 679

Query     1 SALLRSIP   8 (SEQ ID NO: 24) PAS/PAC sensor signal transduction
            SALLR+IP     (SEQ ID NO: 30) histidine kinase Stigmatella aurantiaca
Sbjct   288 SALLRAIP 295 (SEQ ID NO: 25) DW4/3-1

Query     2 ALLRSIP    8 (SEQ ID NO: 21) regulatory protein, LuxR Mariprofundus
            ALLRSIP      (SEQ ID NO: 21) ferrooxydans PV-1
Sbjct   312 ALLRSIP  318 (SEQ ID NO: 21)

Query     2 ALLRSIPA   9 (SEQ ID NO: 20) Tetratricopeptide TPR_2 Herpetosiphon
            ALLR+IPA     (SEQ ID NO: 29) aurantiacus ATCC 23779
Sbjct   189 ALLRTIPA 196 (SEQ ID NO: 26)

Query     2 ALLRSIPA   9 (SEQ ID NO: 20) coenzyme F390 synthetase/phenylacetyl
            ALLRS+PA     (SEQ ID NO: 31) CoA ligase Methanoculleus marisnigri JR1
Sbjct   406 ALLRSVPA 413 (SEQ ID NO: 27)

Query     2 ALLRSIP    8 (SEQ ID NO: 21) metal dependent phosphohydrolase
            ALLRSIP      (SEQ ID NO: 21) Acidobacteria bacterium Ellin345
Sbjct   134 ALLRSIP  140 (SEQ ID NO: 21)
```

Example 2

Assays for Neuroprotective Activity

NATLSIHQ (SEQ ID NO:4) and STPTAIPQ (SEQ ID NO:6) are NAP-like peptides. The effect of these peptides on astrocyte and neuronal survival following $ZnCl_2$ and beta-amyloid intoxication were tested.

A. Methods:

1. Cerebral Cortical Astrocytes

Cell cultures were prepared as previously described (McCarthy KD, de Vellis J., *J. Cell Biol.*, 85:890-902 (1980); Gozes I et al., *J. Pharmacol. Exp. Ther.*, 257:959-66 (1991)). Newborn mice (Harlan Biotech Israel Ltd., Rehovot, Israel) were sacrificed by decapitation and the brain was removed. The cortex was dissected and meninges were removed. The tissue was minced with scissors and placed in Hank's balanced salts solution X1 (HBSS, Biological Industries, Beit Haemek, Israel), 15 mM HEPES Buffer pH 7.3 (Biological Industries, Beit Haemek, Israel) and 0.25% trypsin (Biological Industries, Beit Haemek, Israel) in an incubator at 37° C. 10% $CO_2$ for 20 minutes. The cells were then placed in 8 ml of solution D1 containing 10% heat inactivated fetal calf serum (Biological Industries, Beit Haemek, Israel), 0.1% gentamycin sulphate solution (Biological Industries, Beit Haemek, Israel) and 0.1% penicillin-streptomycin-nystatin solution (Biological Industries, Beit Haemek, Israel) in Dulbecco's modified Eagle's medium (DMEM, Sigma, Rehovot, Israel). The cells were allowed to settle, and were then transferred to a new tube containing 2.5 ml of D1 and triturated using a Pasteur pipette. The process was repeated twice more. Once all the cells were suspended, cell density was determined using a hemocytometer (Neubauer improved, Germany) and $1 \times 10^6$ cells/15 ml D1 were inoculated into each 75 cm$^2$ flask (Corning, Corning, N.Y., USA). Cells were incubated at 37° C. 10% $CO_2$. The medium was changed after 24 hours and cells were grown until confluent (one week).

2. Cerebral Cortical Astrocyte Cell Subcultures

The flasks containing the cerebral cortical astrocytes were shaken to dislodge residual neurons and oligodendrocytes that may be present. Flasks were then washed with 10 ml cold HBSSx1, HEPES15 mM. 5 ml versene-trypsin solution (BioLab, Jerusalem, Israel) was added to each flask and the flasks were incubated at room temperature for 5 minutes to remove astrocytes. The flasks were then shaken to dislodge the cells. The versene-trypsin solution was neutralized with 5 ml D1. The cell suspension was collected and centrifuged at 100 g for 10 minutes. The supernatant was removed and the cells resuspended in D1. The cells were plated in 96 well plates (Corning, Corning, N.Y., USA) (each flask to 2 plates) and incubated until confluent at 37° C. 10% $CO_2$.

3. Mixed Neuroglial Cultures

Newborn rats were used to prepare cerebral cortical astrocytes cell cultures as described above. After suspending the cells in D1, they were centrifuged at 100 g for 5 minutes and the supernatant discarded. The cell pellet was resuspended in solution D2 containing 5% heat inactivated horse serum (Biological Industries, Beit Haemek, Israel), 0.1% gentamycin, 0.1% penicillin-streptomycin-nystatin, 1% N3 (defined medium components essential for neuronal development in culture, (Romijn HJ, *Brain Res.,* 254:583-9 (1981)]), 15 µg/ml 5'-fluoro-2-deoxyuridine (FUDR, Sigma, Rehovot, Israel), and 3 µg/ml uridine (Sigma, Rehovot, Israel) in DMEM. Cells were counted in a hemocytometer, diluted in D2 and 17,000 cells/well/96 well plate were seeded on 8-day-old astrocytes prepared as described above. The medium was changed the next day to D2 without FUDR and uridine. Cells were allowed to grow for one week at 37° C. 10% $CO_2$ before experiments were performed.

4. MAP2 Assay:

Neuronal survival in neuroglial cultures following beta-amyloid intoxication was assayed using the neuron specific antibody, MAP2. One week after the preparation of the mixed neuroglial cultures, the cell growth medium was aspirated and fresh D2 medium was added to the cells. 0.25µM beta-amyloid 1-42(American Peptide Company, Sunnyvale, Ca, USA), dissolved in water and allowed to aggregate for at least two weeks in 37°C, was added to each well together with ascending concentrations of either NATLSIHQ (SEQ ID NO:4) or STPTAIPQ (SEQ ID NO:6) from $10^{-19}$M to $10^{-5}$M. The cells were incubated for 5 days in 10% $CO_2$ at 37°C.

5 days after the addition of beta-amyloid and the peptide, the cells were fixed by removing the media from each well and the addition of cold methanol. The cells were left in the refrigerator overnight. The cells were immunostained with anti-MAP2 as previously described (Brooke S M et al., *Neurosci. Lett.,* 267:21-4(1999)): the methanol was removed and the cells were washed 4 times with phosphate buffered saline (PBS). Blocking for non-specific antibody binding was performed by incubating the cells in 5% non-fat milk in PBS overnight at 4° C. The blocking solution was then removed and anti-MAP2(1:1000; Sigma, Rehovot, Israel) was added to each well. The cells were incubated for 30 minutes at room temperature, followed by 4 washes with PBS. Biotinylated anti-mouse IgG (1:200, Vector Laboratories, Burlingame, Calif., USA) was then added to each well, and the cells were incubated for 30 minutes at room temperature followed by 4 washes with PBS. The cells were incubated at room temperature for 30 minutes with the ABC reagent (Vector Laboratories, Burlingame, Calif., USA) prepared according to the manufacturer's protocol and then washed 4 times with PBS. ABTS reagent, prepared according to the manufacturer's protocol (Vector Laboratories, Burlingame, Calif., USA) was then added to each well and the cells were incubated for 20 minutes in the dark at room temperature. The plates were read in an ELISA plate reader at 405nm. As blanks, wells containing untreated cells and no primary antibody were used.

5. MTS Assay

The survival of astrocytes following intoxication with $ZnCl_2$ was tested using the MTS assay. One week after subculturing the astrocytes into 96-well plates, the astrocyte growth medium was aspirated and fresh medium containing 200µM $ZnCl_2$ and ascending concentrations of NATLSIHQ (SEQ ID NO:4) or STPTAIPQ (SEQ ID NO:6)(concentration range: $10^{-16}$-$10^{-7}$M) was added to the cells. The cells were incubated for 4 hours in 10% $CO_2$ at 37°C., followed by an MTS assay using Celltiter 96 Aqueous non-radioactive cell proliferation assay (Promega, Madison, WI, USA) which was performed according to the manufacturer's instructions and read in an ELISA plate reader at 490nm.

Figure 2:
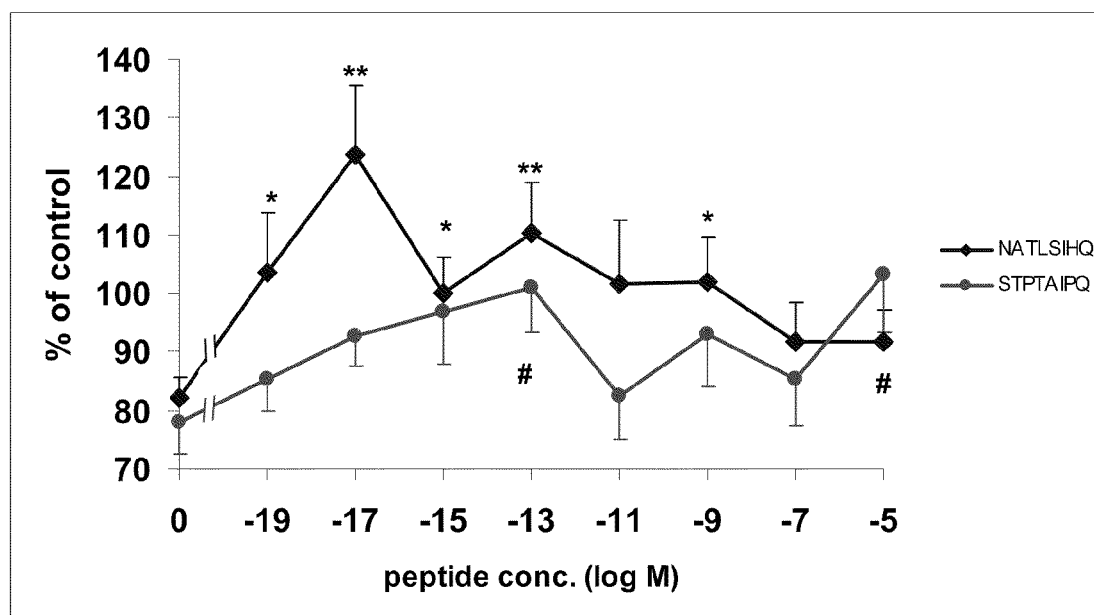
FIG. 2: The effect of peptides on the survival of neuroglial cultures following intoxication with beta-amyloid. The graph depicts 3 experiments per peptide which were each performed in quintuplets. NATLSIHQ (SEQ ID NO:4): *=p<0.05; **=p<0.005; STPTAIPQ (SEQ ID NO:6): #=p<0.05. (In comparison to the negative control—no additions).

B. Results:

Results are shown in FIGS. 1 and 2 and in Table 3, below. Both peptides were active in the neuroprotection assays. The efficacy of NATLSIHQ (SEQ ID NO:4) was greater than that of STPTAIPQ (SEQ ID NO:6) in assays for survival of both neuroglial cells and astrocytes.

TABLE 3 a summary of the effective concentrations of the tested peptides on astrocyte and neuronal survival.

| Peptide: | Neurons (25 µM beta-amyloid) | Astrocytes (200 µM $ZnCl_2$) |
|---|---|---|
| STPTAIPQ (SEQ ID NO: 6) | $10^{-13}$, $10^{-5}$ ($p < 0.05$) | $10^{-7}$ ($p < 0.05$) |
| NATLSIHQ (SEQ ID NO: 4) | $10^{-17}$, $10^{-13}$, ($p < 0.05$) $10^{-19}$ $10^{-15}$ $10^{-9}$ ($p < 0.05$) | $10^{-10}$ ($p < 0.05$) $10^{-12}$, $10^{-8}$ ($p < 0.005$) $10^{-7}$ ($p < 0.0005$) |

Example 3

The Effect of NAPVIPQ and NATLSIHQ on Tau Pathological Aggregation Leading to Neurofibrillary Tangle Formation VQIVYK aggregation: Tau is a highly soluble protein. The unfolded protein lacks a defined 3D structure. Its main role is stabilization of microtubules in neuronal axons. Tau contains three or four microtubule binding repeats. $^{306}$VQIVYK$^{311}$ is a peptide derived from the beginning of the third microtubule binding repeat of tau, which is present in all tau variants. This sequence was found to be important for the aggregation of tau into paired helical filaments (PHFs), which aggregate to make the tangles found in Alzheimer's disease and related disorders.

It is hypothesized that inhibition of tau aggregation will constitute future therapeutics. The aim of this study was to compare NAP alpha-aminoisobutyric acid (where the prolines in NAPVSIPQ were substituted with alpha-aminoisobutyric acid) with NAPVSIPQ containing prolines in an in vitro tau-like aggregation assay.

In vitro aggregation assay was performed in the presence of polyglutamic acid (or heparin), VQIVYK aggregates were further detected by Thioflavin S (excitation 485 nm and emission 535) with emission intensity greatly increasing.

1. Calibration of VQIVYK Aggregation Conditions

Figure 3:
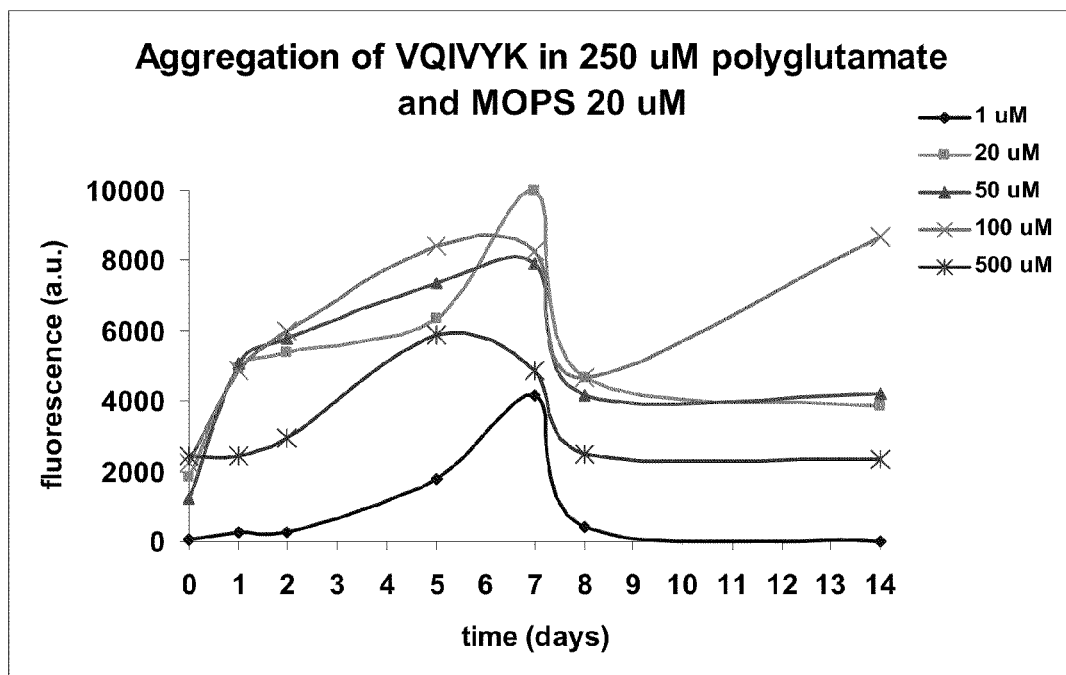
FIG. 3: Time course of VQIVYK aggregation at different concentrations (1-500 μM) in the presence of 250 μM polyglutamate and 20 μM MOPS. Peak aggregation occurs on day 7 with 100 μM VQIVYK in 250 μM polyglutamate and 20 μM MOPS at pH 6.5.

First, different concentrations of polyglutamic acid (0,100 µM, 250 µM, 400 µM) VQIVYK and either sodium acetate (NH$_4$Ac) 50 mM pH 6.5 or MOPS 20 mM pH 6.5 and Thioflavin S 5 µM were mixed together and incubated at room temperature. The extent of aggregation was read at excitation 485 nm and emission 535 nm using the infinite 200 system with the Magellan program. Optimal aggregation conditions were found to be at 7 days with 100 µM VQIVYK, 250 µM polyglutamate and 20 mM MOPS pH 6.5 (see FIG. 3).

Figure 4:
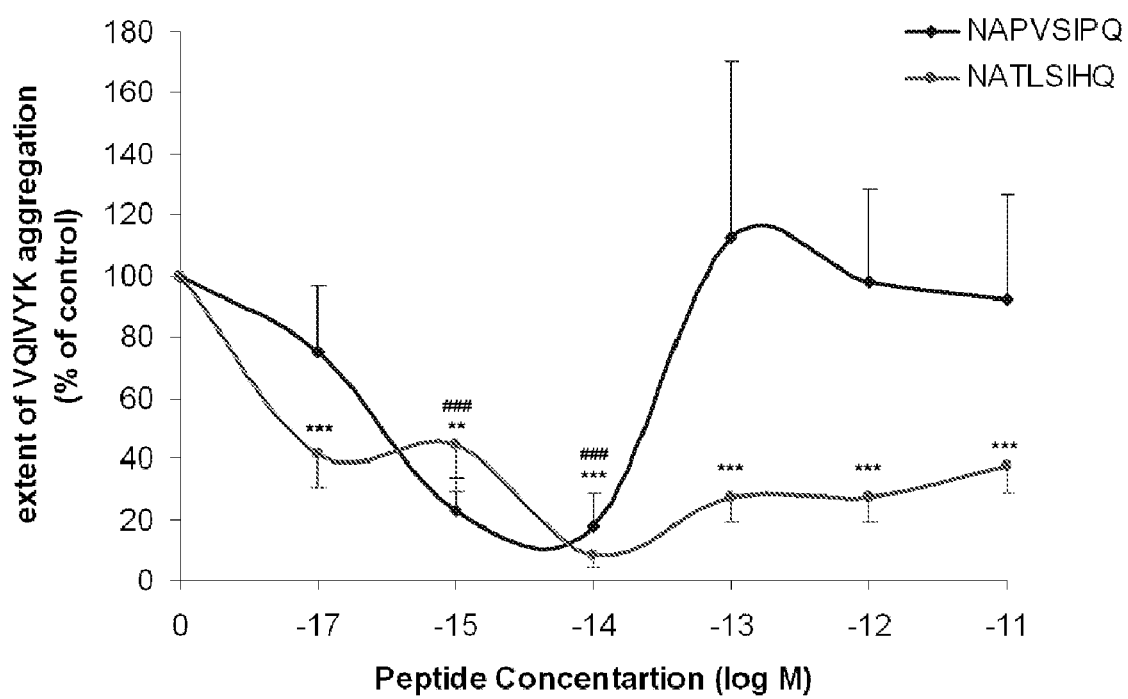
FIG. 4: Effect of peptides NAPVSIPQ and NATLSIHQ on VQIVYK aggregation. NATLSIHQ (SEQ ID NO:4) shows superior effect than NAPVSIPQ (SEQ ID NO:1) in the inhibition of tau aggregation.

2. The Effect of the Peptides NAPVSIPQ (NAP) and NATLSIHQ NAP (isoNAP) on the Extent of VQIVYK Aggregation As shown in FIG. 4, the peptides were added at a range of concentrations ($10^{-17}$ M - $10^{-9}$ M) and the extent of aggregation of 100 µM VQIVYK was tested in the presence of polyglutamate 250 µM in MOPS 20 µM, pH 6.5 for 7 days.

In order to avoid reading self peptide aggregation as VQIVYK aggregation, for each peptide concentration, the fluorescence of the peptide solution without VQIVYK was subtracted from the fluorescence of each peptide concentration containing VQIVYK. NATLSIHQ seems to be superior to NAP in terms of inhibition of tau aggregation adding additional claims and covering protein aggregation diseases.

REFERENCES

1. Friedhoff et al., *Biochemistry*, 1998, 37, 10223-10230.
2. Perez et al., *Journal of Neurochemistry*, 2007, 103, 1447-1460.
3. von Bergen et al., *PNAS*, 2000, 97, 5129-5134.

Example 4

The Effect of Treatment with NAT on Learning and Memory in Tau Transgenic Mice: An Animal Model for Human Tauopathy Materials and Methods
Animals The mouse model, used in the current study, was previously described (Ramsden et al., (2005) *J Neurosci*, 25, 10637-10647). The rTg(tauP301L)4510 mouse (designated as Tau-Tg below) expresses the human 4-repeat Tau with the P301L mutation (4RON) associated with frontotemporal dementia and Parkinsonism linked to chromosome 17.

In this mouse model, levels of several soluble phosphorylated tau species were highest at 1 month relative to later time points, this material was cleared by 3 months, while heat shock protein expression increased with normal aging. This process was accelerated in rTg4510 mice. Moreover, endogenous mouse tau turnover was slowed in response to human tau over-expression, and this endogenous tau adopted disease-related properties (Dickey et al., (2009) *Am J Pathol*, 174, 228-238). The onset of memory deficit was first observed at 2.5 months and was significant at 4 months. Mature neurofibrillary tangles, detected by Bielschowsky silver stain, appeared at 4 months and significant neuronal loss was estimated by stereology at 5.5 months (Ramsden et al., (2005) *J Neurosci*, 25, 10637-10647).

The experiment included three groups: Tau-Tg female mice, 10-month-old, treated by intranasal administration of NAT 2 µg/5 µl/mouse/day (n=5) or vehicle (SW/mouse/day) (n=6), and as control, non-Tg female littermates treated by vehicle (SW/mouse/day) (n=7).

NAT (NATLSIHQ) Administration

NAT was dissolved in a vehicle solution, in which each milliliter include 7.5 mg of NaCl, 1.7 mg of citric acid monohydrate, 3 mg of disodium phosphate dehydrate, and 0.2 mg of benzalkonium chloride solution (50%). 5 µl of NAT or vehicle solution (DD) were administered intranasally.

Treatment started at 9 months of age and continued daily for a period of 5 weeks. At each test NAT was applied 1 h before the test begun.

Comparative analysis between vehicle-treated transgenic and vehicle-treated non-Tg mice allowed evaluation of the pathology associated with the expression of the human mutant tau. By comparing Tau-Tg NAT-treated mice and vehicle-treated mice peptide efficacy was tested.

All mice were weighed at the beginning and end of the experiment and whole brain weight was measured before the brain dissection.

Behavioral Testing —Morris Water Maze (MWM)

Each mouse was placed in a pool of water that is colored opaque with powdered non-fat milk, where it must swim to a hidden escape platform. The position of the platform was altered between days but remained constant within each day.

Test conditions: Pool diameter—on days 1-3: 80 cm and on days 4-5: 140 cm. Platform—clear plaxiglass, 12 cm in diameter, 2 cm below the surface of the water. Water temperature—22° C.-23° C., Room temperature—26-28° C.

Experimental procedure: Mice were treated with NAT or vehicle and then habituated for 1 hour in the experiment room. The tested mouse was placed on the platform for 30 seconds followed by 2 sequential trials with a cut-off of 90 seconds and an Intra Experimental Interval (IEI) of 30 seconds in which it stayed on the platform. The time required for reaching the platform in each trial and the path lengths were measured.

On the fifth day, two additional tests were taken after the second daily trial:

1. Probe test—The platform was removed from the maze. The mouse was released at the same place in the pool as on the prior trial and the time the mouse spent in the quarter in which the platform was situated on the prior trial was recorded.

2. Visible platform test—In order to verify that all mice are capable of seeing the platform was placed in the center of the pool, 1 cm above the water surface. The mice passed the visible platform test.

Biochemical Analysis

Mouse brain tissue was rapidly dissected and quickly separated into four different brain sections: cortex, hippocampus, cerebellum and rest of the brain. Brains were kept frozen at −80° C. for further biochemical analysis. Total levels of nuclear ADNP were analyzed by immunoblotting. Cerebral cortex samples (~50 mg each) were homogenized and cytoplasmic and nucleus proteins were separated using lysis buffer (20 mM TRIS HCl pH 7.7, mM KCl, 0.1 mM EDTA, 1.5 mM MgCl2, 0.2% NP-40) and extraction buffer (10 mM TRIS HCl pH 7.7, 0.1 mM EDTA, 1.5 mM MgCl2, 20% Glycerol, 1.61 gr NaCl). Protein amount was estimated and corrected by using the Bradford assay and then separated by electrophoresis on 12% polyacrylamide gels containing SDS (Shiryaev et al., (2009) *Neurobiol Dis*, 34, 381-388). Western blot analyses were performed by applying brain protein samples onto two gels. Each gel had sample representation from each one of the three groups. The proteins were transferred to nitrocellulose filter and immunostained with ADNP specific antibody (BD Bioscience, 1/300). Proteins were visualized using enhanced chemiluminescence reagents, followed by exposure onto hyperfilm (Kodak) (Mandel and Gozes (2007) *J Biol Chem*, 282, 34448-34456). Protein bands on hyperfilm were quantified using photochromatography analysis. The ADNP amount in each band was calculated as its percentage from the total amount of all bands. ADNP amounts of each group were averaged.

Statistical Analyses

Results are described as means+standard error (S.E.). Initial statistical analyses compared only two groups among the three and included two-tailed indipendent t-tests. P values of 0.05 were deemed statistically significant. Additional statistical analyses were performed using One-way ANOVA to compare the three experimental groups followed by Tukey's Honestly Significantly Different (HSD) post-hoc test.

Results

Tau Transgenic Mice Exhibited Deficit in Spatial Learning and Working Memory

At the third experimental week, mice treated daily with NAT or vehicle were subjected to two daily tests for five executive days in the Morris water maze (MWM) that evaluates spatial learning and working memory.

Figure 5:
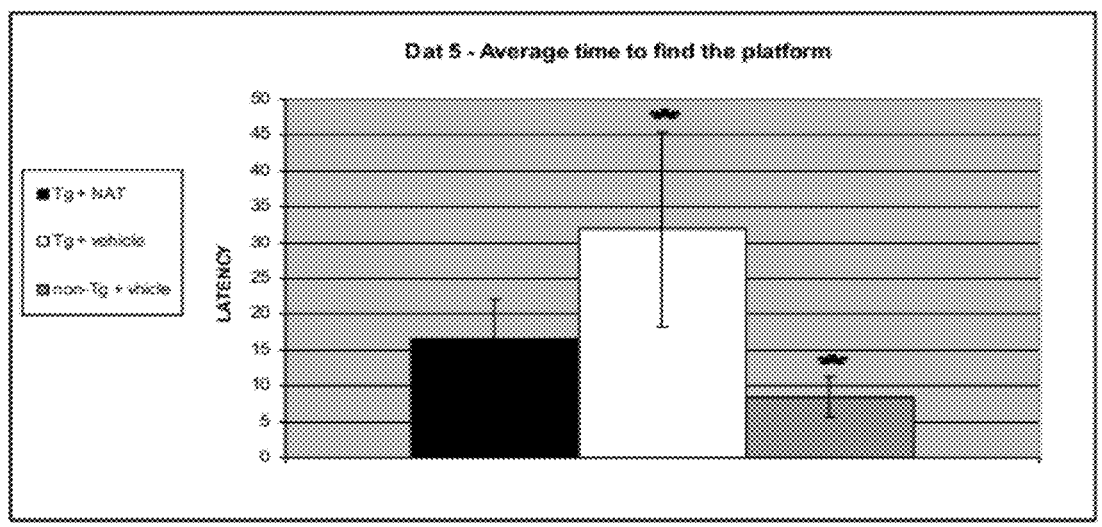
FIG. 5: The Morris water maze results on Day 5 between the non-Tg mice and the Tau-tg vehicle treated mice show a statistically marginally significant difference.

Latencies to find the hidden platform were measured daily and the results of the second daily test (that evaluates working memory) were averaged per group. On the fifth day (Day 5) of the Morris water maze (shown in FIG. 5) there was a statistically marginally significant difference (p<0.075, one tailed t-test) between the non-Tg mice and the Tau-tg vehicle treated mice [8.45±2.87 sec; n=7 vs. 31.88±13.54 sec; n=6; respectively, mean±S.E.]

Figure 6:
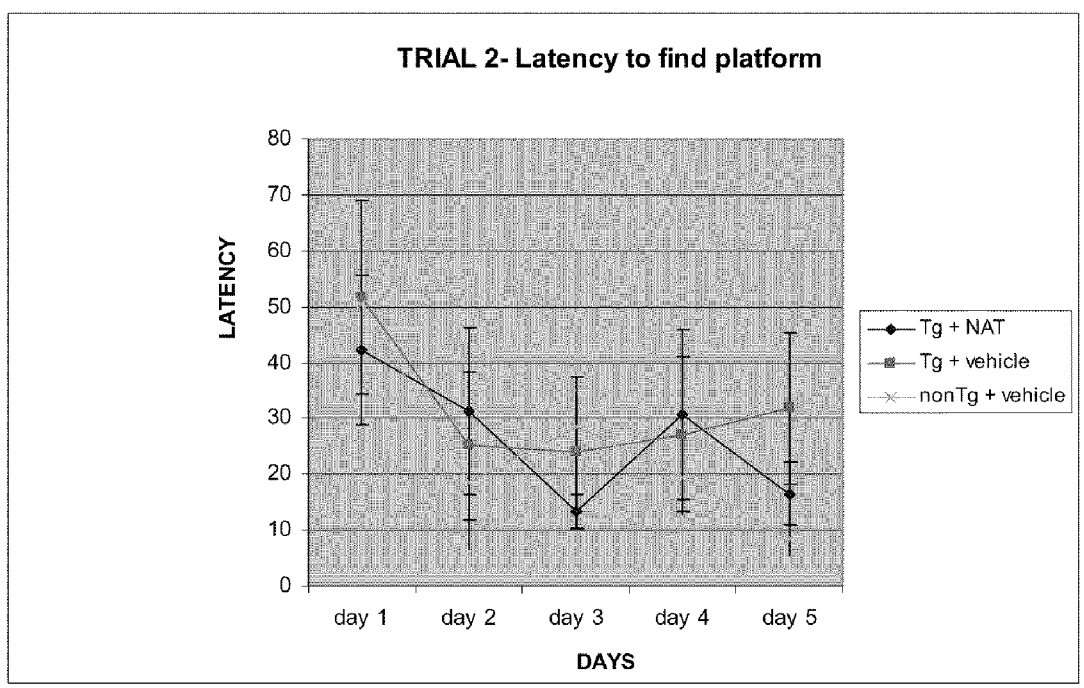
FIG. 6: Latency to find the hidden platform during the second daily trial. The improvement in learning was analyzed using t-tests for dependent samples that compared for each group the latency to find the platform on the first day and on the fifth day of the MWM. Significant improvement was found in the Tau-Tg NAT treated group (p=0.039) and for the non-Tg group (p=0.007).

Importantly, the improvement in learning was analyzed using t-tests for dependent samples that compared for each group the latency to find the platform on the first day and on the fifth day of the MWM (a learning curve). Significant improvement was found in the Tau-Tg NAT treated group (p=0.039) and for the non-Tg group (p=0.007), suggesting a cognitive improvement upon treatment with NAT in the "tauopathy"—afflicted mice (FIG. 6).

NAT Treatment Increased Brain-Body Weight Ratio of the TAU-Tg Mice

All mice were weighed before first drug application and again before the dissection (while still alive). Body weights before and after treatment were compared by t-test for repeated measures and no statistical difference was found (p=0.98). Whole brain was weighed before the brain sections were separated and no significant statistical differences between the groups were found. However, Brain-Body weight ratio may be used to measure brain mass decrease possibly indicating neuronal degradation (Bassan et al., (2009) *J Matern Fetal Neonatal Med*, 1-6).

Figure 7:
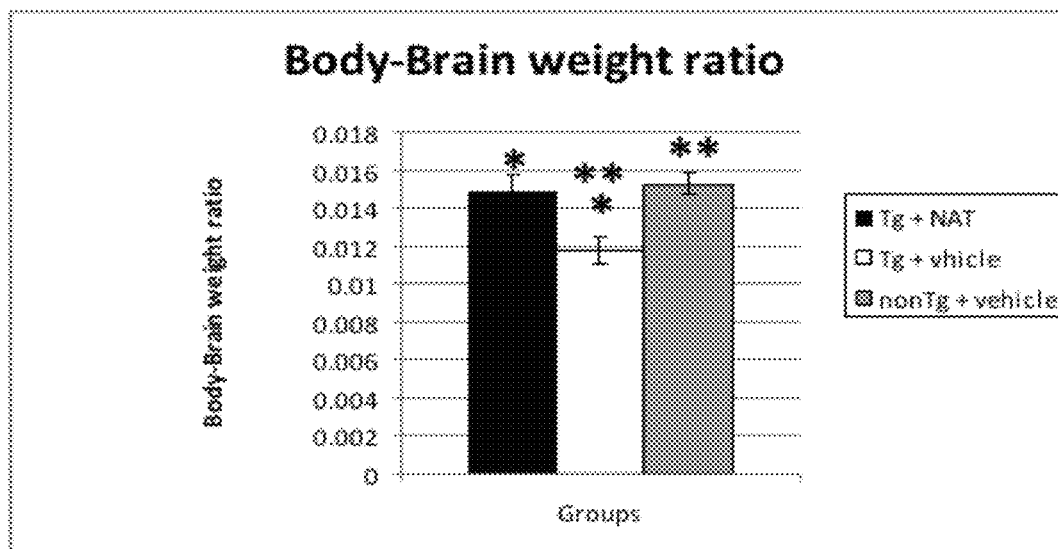
FIG. 7: Brain-Body weight ratios show protective effect of NAT treatment from neurodegeneration.

Brain-Body weight ratio was calculated for each mouse and averaged per group [TAU-Tg+NAT 0.0148+0.0009, TAU-Tg+Vh 0.0117+0.0007, w.t. control 0.0152+0.0005]. The difference between group averages was confirmed by one way ANOVA that showed a significant difference between the three experimental groups with p=0.006. Tukey HSD post-hoc test showed a significant difference between the NAT and vehicle treated TAU-Tg groups (p=0.030) and between the non-Tg. and the vehicle treated Tau-tg animals (p=0.007). NAT treated Tg mice were not different from the non-Tg group (p=0.909) suggesting that NAT treatment protected the brain from neurodegeneration (FIG. 7).

Increase in the Relative Amount of Nuclear ADNP in NAT Treated TAU-Tg Mice

ADNP (Activity-Dependent Neuroprotective Protein) is a protein highly expressed in the brain as well as other tissues and shown to be secreted from glial cells and further involved in neuroprotection in a variety of cytotoxic damages. It had been shown that ADNP expression is correlated with the need of brain protection (Gozes (2007) *Pharmacol Ther*, 114, 146-154).

In this study, mouse endogenous ADNP levels were quantified by immunoblotting with ADNP specific antibodies. One way ANOVA analysis showed a significant difference between the three experimental groups (p=0.0079). Tukey HSD post-hoc test revealed a difference between the NAT and vehicle treated TAU-Tg groups (p=0.0028) and between the vehicle treated TAU-Tg and non-TG group (p=0.0097) (FIG. 8).

Figure 9:
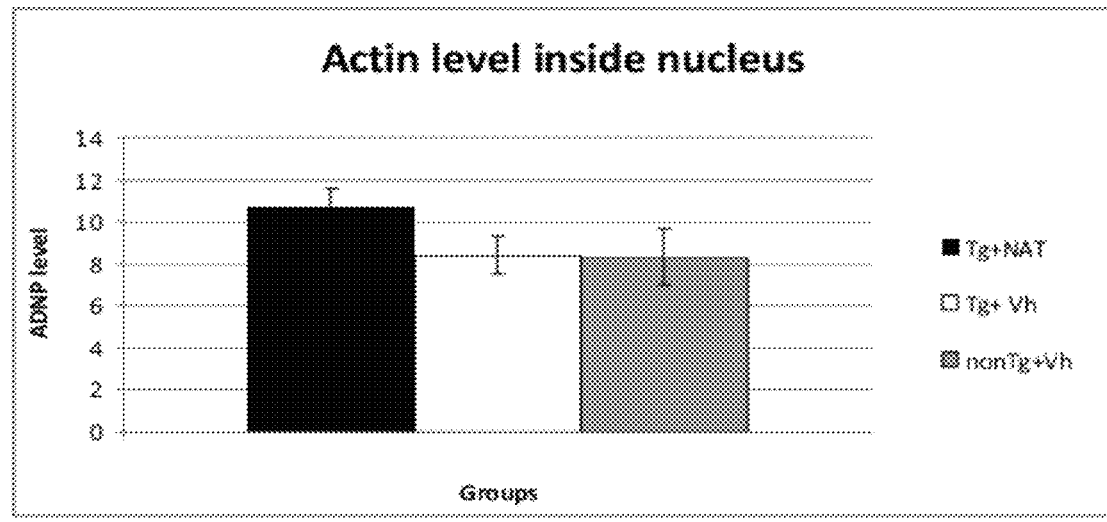
FIG. 9: NAT treatment leads to no significant change in the amount of actin in cell nucleus.

Worthy of note, ADNP levels in non-Tg mice are as high as in NAT treated mice. This high level could be related to the degree of brain protection. However, actin was used also (FIG. 9) and showed no statistical difference among the tested groups.

It will be appreciated that this invention describes a new class of tubulin-binding peptide mimetics, including those comprising peptides with similarity to NAP or SAL for providing neurotrophic and neuroprotective activity and potential additional therapeutic activities. Modifications include conventional replacements, addition of 40 amino acid N- or C-terminal, lipophylization, acetylation etc.

The examples set out above are intended to be exemplary of the effects of the invention, and are not intended to limit the embodiments or scope of the invention contemplated by the claims set out below. Other variants of the invention will be readily apparent to one of ordinary skill in the art and are encompassed by the appended claims. All publications, databases, Genbank sequences, GO terms, patents, and patent applications cited in this specification are incorporated by reference in their entireties, as if each individual publication or patent application were specifically and individually indicated to be incorporated by reference.

What is claimed is:

1. A peptide mimetic consisting of the amino acid sequence of formula $$(R^1)_a—(R^2)—(R^3)_b$$

wherein:
R$^1$ is an amino acid sequence cosisting of 1 to 40 amino acids wherein each amino acid is independently selected from the group consisting of naturally occurring amino acids and amino acid analogs;
R$^2$ is NATLSIHQ (SEQ ID NO:4);
R$^3$ is an amino acid sequence consisting of 1 to 40 amino acids wherein each amino acid is independently selected from the group consisting of naturally occurring amino acids and amino acid analogs;
a and b are independently selected and are equal to zero or one;
wherein none or as many as all of the amino acids in the peptide mimetic are in the D configuration; and
with the proviso that the peptide mimetic does not comprise the sequence NAPVSIPQ (SEQ ID NO:1) or SALLRSIPA (SEQ ID NO:19).

2. The peptide mimetic of claim 1, wherein at least one amino acid of R$^2$ is a D-amino acid.

3. The peptide mimetic of claim 1, wherein each amino acid of R$^2$ is a D-amino acid.

4. A peptide mimetic consisting of the amino sequence of formula $$(R^1)_a—(R^2)—(R^3)_b$$

and at least one protecting group,
wherein:
R$^1$ is an amino acid sequence consisting of 1 to 40 amino acids wherein each amino acid is independently selected from the group consisting of naturally occurring amino acids and amino acid analogs;
R$^2$ is NATLSIHQ (SEQ ID NO:4);

R³ is an amino acid sequence consisting of 1 to 40 amino acids wherein each amino acid is independently selected from the group consisting of naturally occurring amino acids and amino acid analogs;

a and b are independently selected and are equal to zero or one;

wherein none or as many as all of the amino acids in the peptide mimetic are in the D configuration; and with the proviso that the peptide mimetic does not comprise the sequence NAPVSIPQ (SEQ ID NO:1) or SALLRSIPA (SEQ ID NO: 19).

5. The peptide mimetic of claim 1, wherein the peptide mimetic is NATLSIHQ (SEQ ID NO:4).

6. The peptide mimetic of claim 5, wherein at least one amino acid is a D-amino acid.

7. The peptide mimetic of claim 5, wherein each amino acid is a D-amino acid.

8. A peptide mimetic consisting of the amino acid sequence NATLSIHQ (SEQ ID NO:4) and at least one protecting group.

9. A pharmaceutical composition comprising the peptide mimetic of claim 1.

10. The pharmaceutical composition of claim 9, further comprising a neuroprotective polypeptide comprising an amino acid sequence selected from the group consisting of NAPVSIPQ (SEQ ID NO:1) and SALLRSIPA (SEQ ID NO:19).

* * * * *